US009862939B2

United States Patent
Radin et al.

(10) Patent No.: US 9,862,939 B2
(45) Date of Patent: Jan. 9, 2018

(54) PLANT LECTINS AS CARRIERS OF ASSOCIATED DRUG SUBSTANCES INTO ANIMAL AND HUMAN CELLS

(71) Applicant: BIOSTRATEGIES LC, State University, AR (US)

(72) Inventors: David N. Radin, Jonesboro, AR (US); Carole L. Cramer, Jonesboro, AR (US)

(73) Assignee: BIOSTRATEGIES LC, State University, AR (US)

( * ) Notice: Subject to any disclaimer, the term of this patent is extended or adjusted under 35 U.S.C. 154(b) by 0 days.

(21) Appl. No.: 14/956,001

(22) Filed: Dec. 1, 2015

(65) Prior Publication Data
US 2016/0083707 A1    Mar. 24, 2016

Related U.S. Application Data

(63) Continuation of application No. 13/906,203, filed on May 30, 2013, now abandoned.

(60) Provisional application No. 61/653,062, filed on May 30, 2012.

(51) Int. Cl.
| | |
|---|---|
| *C12N 9/24* | (2006.01) |
| *C07K 16/16* | (2006.01) |
| *C07K 14/54* | (2006.01) |
| *C12N 9/14* | (2006.01) |
| *A61K 47/48* | (2006.01) |
| *A61K 47/64* | (2017.01) |
| *A61K 38/00* | (2006.01) |

(52) U.S. Cl.
CPC ...... *C12N 9/2497* (2013.01); *A61K 47/48261* (2013.01); *A61K 47/6415* (2017.08); *C07K 14/5434* (2013.01); *C07K 16/16* (2013.01); *C12N 9/14* (2013.01); *C12N 9/2402* (2013.01); *A61K 38/00* (2013.01); *C07K 2317/76* (2013.01); *C07K 2319/00* (2013.01); *C07K 2319/02* (2013.01); *C12Y 302/01076* (2013.01); *C12Y 302/02022* (2013.01); *C12Y 310/01001* (2013.01)

(58) Field of Classification Search
None
See application file for complete search history.

(56) References Cited

U.S. PATENT DOCUMENTS

| | | | |
|---|---|---|---|
| 4,938,949 A | 7/1990 | Borch et al. | |
| 5,034,322 A | 7/1991 | Rogers et al. | |
| 5,106,739 A | 4/1992 | Comai et al. | |
| 5,589,610 A | 12/1996 | De Beuckeleer et al. | |
| 5,625,136 A | 4/1997 | Koziel et al. | |
| 5,639,948 A | 6/1997 | Michiels et al. | |
| 5,661,017 A | 8/1997 | Dunahay et al. | |
| 5,705,484 A | 1/1998 | Thomason | |
| 5,929,304 A | 7/1999 | Radin et al. | |
| 6,455,760 B1 | 9/2002 | Zhao et al. | |
| 6,462,185 B1 | 10/2002 | Takakura et al. | |
| 6,696,623 B1 | 2/2004 | Doerner et al. | |
| 6,884,419 B1 | 4/2005 | Yokoi et al. | |
| 7,011,972 B2 | 3/2006 | Barbas, III et al. | |
| 7,410,779 B2 | 8/2008 | Fleer et al. | |
| 7,858,576 B2 | 12/2010 | LeBowitz et al. | |
| 7,867,972 B2 | 1/2011 | Ballance et al. | |
| 7,964,377 B2 | 6/2011 | Papadopoulos et al. | |
| 2003/0084486 A1 | 5/2003 | Bruce et al. | |
| 2003/0177536 A1 | 9/2003 | Grundler et al. | |
| 2004/0019934 A1 | 1/2004 | Ekramoddoullah et al. | |
| 2004/0067506 A1 | 4/2004 | Scheres et al. | |
| 2004/0078841 A1 | 4/2004 | Atkinson et al. | |
| 2004/0123349 A1 | 6/2004 | Xie et al. | |

FOREIGN PATENT DOCUMENTS

| | | |
|---|---|---|
| EP | 1528104 | 5/2005 |
| WO | WO 2005/009394 | 2/2005 |
| WO | WO 2008-157263 | 12/2008 |

OTHER PUBLICATIONS

Acosta, W. et al., "Molecular Pharming: a renewable resource for bioproduction of high value therapeutic proteins," poster presented at 22nd National NSF EPSCoR Conference, Oct. 24, 2011.

Cai, Q. et al., "Lectin-mediated cytotoxicity and specificity of 5-fluorouracil conjugated with peanut agglutinin (5-Fu-PNA) in vitro," *Journal of Drug Targeting*, 2005, vol. 13, No. 4, pp. 251-257.

Wirth, M. et al., "Lectin-Mediated Drug Targeting: Preparation, Binding Characteristics, and Antiproliferative Activity of Wheat Germ Agglutinin Conjugated Doxorubicin on Caco-2 Cells," *Pharmaceutical Research*, 1998, vol. 15, No. 7, pp. 1031-1037.

Bevan, M. et al. "The structure and transcription start site of a major potato tuber protein gene" *Nucleic Acid Res.*, 1986, 14(11):4625-4638.

Bie, H. et al. "Insights into mucopolysaccharidosis I from the structure and action of α-L-iduronidase" *Nat. Chem. Biol.*, 2013, 9(11):739-745.

Chen, X. et al. "Design of an in vivo cleavable disulfide linker in recombinant fusion proteins" *BioTechniques*, 2010, 49:513-518.

(Continued)

*Primary Examiner* — Paul J Holland
(74) *Attorney, Agent, or Firm* — Saliwanchik, Lloyd & Eisenschenk

(57) ABSTRACT

The current invention involves the use of protein lectins produced by plants including the non-toxic carbohydrate binding subunits (B subunits) of plant "AB toxins" (PTB lectins) as delivery vehicles for mobilizing associated drug substances for delivery to animal and human cells. The resulting protein fusions or conjugates retain lectin carbohydrate specificity for binding to cells and cellular trafficking activity so as to deliver an associated drug compound to the site of disease manifestation. One embodiment of this invention concerns the ability of ricin toxin B subunit, as a model PTB lectin, to deliver enzyme replacement therapeutic drugs to cells of several organs of the body including the brain and central nervous system, eyes, ears, lungs, bone, heart, kidney, liver, and spleen for treating lysosomal diseases.

19 Claims, 5 Drawing Sheets

(56) References Cited

OTHER PUBLICATIONS

Citores, L. et al. "Differential sensitivity of HELA cells to the type 2 ribosome-inactivating proteins ebulin l, nigrin b and nigrin f as compared with ricin" *Cell. Molec. Biol.*, 1996, 42(4):473-476, abstract only.
Citores, L. et al. "Evidence for distinct cellular internalization pathways of ricin and nigrin b" *Cell. Molec. Biol.*, 2003, 49:OL461-OL465, abstract only.
Förster, C. "Tight junctions and the modulation of barrier function in disease" *Histochem. Cell Biol.*, 2008, 130:55-70.
Lovrinovic, M. and Niemeyer, C. "Rapid synthesis of DNA—cysteine conjugates for expressed protein ligation" *Biochem. Biophys. Res. Comm.*, 2005, 335:943-948.
Lungwitz, U. et al. "Polyethylenimine-based non-viral gene delivery systems" *Eur. J. Pharma. Biopharma.*, 2005, 60:247-266.
Matz, M. et al. "Fluorescent proteins from nonbioluminescent Anthozoa species" *Nat. Biotechnol.*, 1999, 17(10):969-973.
Maveyraud, L. et al. "Structural basis for sugar recognition, including the Tn carcinoma antigen, by the lectin SNA-II from *Sambucus nigra*" Proteins, 2009, 75:89-103.
Medrano, G. et al. "Rapid system for evaluating bioproduction capacity of complex pharmaceutical proteins in plants" In *Methods in Molecular Biotechnology: Recombinant Proteins from Plants*, Faye, L. and Gomord, V. eds., Humana Press, USA, 2009, Chapter 4, pp. 51-67.
Montfort, W. et al. "The three-dimensional structure of ricin at 2.8Å" *J. Biol. Chem.*, 1987, 262(11):5398-5403.
Ohmi, K. et al. "Activated microglia in cortex of mouse models of mucopolysaccharidoses I and IIIB" *Proc. Natl. Acad. Sci. USA*, 2003, 100(4):1902-1907.
Pastores, G. "Enzyme therapy for the lysosomal storage disorders: principles, patents, practice and prospects" *Expert Opin. Ther. Patents*, 2003, 13(8):1157-1172.
Rajendran, L. et al. "Subcellular targeting strategies for drug design and delivery" *Nature Reviews Drug Discovery*, 2010, 9(1):29-42.
Reidy, M. "Engineering of the RTB Lectin as a Carrier Platform for Proteins and Antigens" Dissertation for Doctor of Philosophy in Plant Physiology, Pathology, and Weed Science, Virginia Polytechnic Institute and State University, 2007.
Sandvig, K. and Van Deurs, B. "Endocytosis and intracellular transport of ricin: recent discoveries" *FEBS Letters*, 1999, 452(1-2):67-70.
Scott, H. et al. "Human alpha-L-iduronidase: cDNA isolation and expression" *Proc. Natl. Acad. Sci. USA*, 1991, 88(21):9695-9699.
Simmons, B. et al. "Mannose receptor-mediated uptake of ricin toxin and ricin A chain by macrophages" *J. Biol. Chem.*, 1986, 261(17):7912-7920.
Van Damme, E. et al. "Characterization and molecular cloning of *Sambucus nigra* agglutinin V (nigrin b), a GalNAc-specific type-2 ribosome-inactivating protein from the bark of elderberry (*Sambucus nigra*)" *Eur. J. Biochem.*, 1996, 237(2):505-513.
Van De Kamp, J.J. et al. "Genetic heterogeneity and clinical variability in the Sanfilippo syndrome (types A, B, and C)" *Clin. Genet.* 1981, 20(2)152-160, abstract only.
Winchester, B. et al. "The molecular basis of lysosomal storage diseases and their treatment" *Biochem. Soc. Trans.*, 2000, 28(2):150-154.
Accession No. 1G7K_A (version GI:12084491), Chain A, Crystal Structure of Dsred, A Red Fluorescent Protein From Discosoma Sp. Red., Oct. 10, 2012.
Accession No. 1G7K_B (version GI:12084492), Chain B, Crystal Structure of Dsred, A Red Fluorescent Protein From Discosoma Sp. Red., Oct. 10, 2012.
Accession No. 1G7K_C (version Gl12084493), Chain C, Crystal Structure of Dsred, A Red Fluorescent Protein From Discosoma Sp. Red., Oct. 10, 2012.
Accession No. 1G7K_D (version GI:12084494), Chain D, Crystal Structure of Dsred, A Red Fluorescent Protein From Discosoma Sp. Red., Oct. 10, 2012.
Accession No. 2AAI_B (version GI:494727), Chain B, Crystallographic Refinement of Ricin to 2.5 Angstroms, Aug. 14, 2013.
Accession No. AAA81589, alpha-L-iduronidase (*Homo sapiens*), Nov. 22, 1995.
Accession No. CAA27588 (version GI:21514), patatin (*Solanum tuberosum*), Nov. 14, 2006.
Accession No. NP_000190 (version GI:4506919), N-sulphoglucosamine sulphohydrolase precursor (*Homo sapiens*), May 3, 2014.
Accession No. P33183 (version GI:17433713), Nigrin B, Agglutinin V, SNAV, Nigrin B, A chain, rRNA N-glycosidase, Nigrin B, B chain (Sambucus nigra), Oct. 1, 2014.
Accession No. pdb/4MJ4, Human iduronidase apo structure P21 form, Sep. 18, 2013.

PLANT LECTINS AS CARRIERS OF ASSOCIATED DRUG SUBSTANCES INTO ANIMAL AND HUMAN CELLS

CROSS-REFERENCE TO RELATED APPLICATIONS

The present application is a continuation of U.S. application Ser. No. 13/906,203, filed May 30, 2013, now abandoned, which claims the benefit of U.S. Provisional Application Ser. No. 61/653,062, filed May 30, 2012, each of which is hereby incorporated by reference herein in its entirety, including any figures, tables, nucleic acid sequences, amino acid sequences, or drawings.

BACKGROUND OF THE INVENTION

Human and animal diseases can often be treated by supplying drug substances that correct disease symptoms by supplying a biochemical substance not made properly by the body. Examples include but are not limited to enzyme replacement therapies (ERTs) for the treatment of Lysosomal Diseases (LDs) like Hurlers Syndrome (MPS I) or Alzheimer's with corrective enzymes for these genetic or age related developmental diseases. These types of diseases are associated with failure of metabolic processes or function of specific cells and biochemical pathways within the body. A goal of many drug advancement programs is, therefore, focused on directing drugs more efficiently to the specific cells or tissues that are responsible for these functions. And the discovery described in this patent application is directed toward facilitating this goal.

Many plants produce specific carbohydrate binding lectins, agglutinins, and toxalbumins which are "AB" toxins that comprise a toxic A subunit protein (e.g., a ribosome-inactivating protein) and a non-toxic B subunit that is typically a lectin (carbohydrate binding protein) responsible for binding to the target cell surface, triggering endocytosis, and mediating intracellular trafficking. A classic example of this AB class of toxins is ricin toxin (from Castor beans) which incorporates a ricin A subunit (RTA) having ribosome-inactivating activity and a ricin B subunit (RTB) having galactose- and galactosamine-binding activity that directs cell uptake and trafficking. As with other AB toxins, the lectin binding capacity of cell surfaces allows binding with carbohydrate binding domains of lectin sequences on the RTB subunit of Ricin triggering endocytosis of the toxin into the cell and transcytosis of the toxin across cell layers by several different mechanisms including Receptor-Mediated Transcytosis (RMT) and Adsorptive-Mediated Transcytosis (AMT).

The development of effective therapeutic drugs to treat many diseases that produce significant impairment of cellular and metabolic function would be facilitated by the discovery of new ways to deliver these drugs to sites of disease pathology in cells and organs of the body. Lysosomal Diseases (LDs), also commonly called lysosomal storage diseases (LSDs) are representative of this class of diseases. LDs are a group of approximately 50 rare inherited metabolic disorders that result from defects in lysosomal function (Winchester et al. (2000)). Lysosomal storage diseases result when a specific organelle in the body's cells—the lysosome—malfunctions. Lysosomal storage disorders are caused by lysosomal dysfunction often as a consequence of deficiency of a single enzyme required for the metabolism of both large molecules or small compounds such as lipids, glycoproteins (sugar containing proteins) or so-called mucopolysaccharides. The lysosome is commonly referred to as the cell's recycling center because it reprocesses or catabolyzes metabolic waste material into substances that the body can recycle into useful substances or eliminate though the kidneys and urinary tract. Lysosomes break down this waste matter via enzymes that are highly specialized proteins that perform most of the chemical reactions essential for cellular functions. Lysosomal disease disorders are triggered when a particular enzyme is defective and suffers from loss of function or is present in too small amounts to perform normal metabolic functions or is missing altogether. When this happens, waste substances may build up to toxic levels that interfere with normal healthy metabolism leading to serious disease symptoms and even death.

Defects in cellular metabolic machinery caused by genetic mutations of lysosomal enzyme genes are a major cause of LDs and are usually expressed in all cells of the body. The level of threat to life of genetically defective lysosomal enzymes varies, however, depending on how much the mutation reduces the function of a particular enzyme and what bodily functions are most impaired. Research during the last few decades has led to the development of effective enzyme replacement (ERT) therapeutics drugs whereby defective enzymes in LD patients are replaced by intravenous delivery of normal enzymes produced by recombinant manufacturing technologies. Although these drugs are now available for a half a dozen of LDs their effectiveness in reducing disease symptoms varies depending on which cells and organs are affected, the severity of symptoms, and the stage of disease progression. Current drugs are more effective in certain organs such as liver and spleen but often much less effective in treating symptoms in such organs as bone, heart, lungs, kidneys, and the CNS (central nervous system) including brain where severe symptoms occur in many LDs. The invention described in this patent is designed to more effectively target ERT's to these recalcitrant organs and also improve treatments in organs such as liver where current therapies could use improvement.

Poor brain development and neural degeneration of the brain and CNS are some of the most devastating symptoms in LDs. The effect of LDs on brain function has been well studied and is a representative example of currently untreatable symptoms of LDs. Homeostasis of the central nervous system (CNS) microenvironment is essential for its normal function. It is maintained by the blood-brain barrier (BBB) which regulates the transport of molecules from blood into brain and backwards. The function of this highly specialized barrier is to (1) protect the brain from blood-borne substances that are potentially detrimental to brain function and (2) to provide nutrients and other required substances to the brain parenchyme by specialized transport systems. The main structures responsible for this barrier property are the tight junctions (TJ). TJ are highly developed in endothelial cells of the brain and CNS vasculature but only moderately formed between endothelial cells of the peripheral vasculature: leaky blood capillaries in the body allow many molecules to cross through to tissue, but the TJ construction of the vessels in the CNS guards against this less restricted entry to the brain (Förster (2008)).

The tight control in transport of chemicals and proteins across the BBB poses a significant challenge to the delivery of diagnostic/therapeutic proteins, nucleic acids, and other drugs to the brain. Small molecules such as lipophilic drugs, gases, glucose, and essential nutrients cross the BBB by a number of passive and active transport mechanisms. In contrast, macromolecules such as proteins and nucleic acids are generally excluded from the brain and only a selective subset of proteins is transported across the BBB using either Receptor-Mediated Transcytosis (RMT) or Absorptive-Mediated Transcytosis (AMT). For substances transported via RMT mechanisms, a specific receptor (e.g., the insulin receptor or the transferrin receptor) is present on the luminal surface of the CNS endothelial cells which mediates uptake, transcytosis, and release of proteins or other therapeutic substances at the abluminal or basal surface where they can access the glial and neuronal cells of the brain. RMT mechanisms are "saturable" and the amount of product and rate by which substances can be mobilized across the BBB are limited by the number of available receptors present on the luminal surface.

In contrast to RMT mechanisms, Absorptive-Mediated Transcytosis (AMT) is independent of specific receptors and involves the binding of specific proteins or substances to the endothelial cell surface by interactions that trigger endocytosis and vesicular trafficking such that a proportion of the endocytosed substance is carried across the endothelial cell layer and subsequently released on the basal/abluminal side providing access to cells of the CNS. The selectivity and control of AMT mechanisms are not well understood but proteins such as cationated albumin and the TAT protein of HIV are known to enter the brain by this mechanism. AMT is considered non-saturable and may have the potential to deliver 10-fold greater amounts of product across the BBB compared to transport via the RMT. The present invention has the advantage that it can utilize multiple trans-cellular transport mechanisms including the AMT and RMT systems.

Role of Lectin in Toxicity of the AB Toxins Such as Ricin:

Many plant derived AB toxins are toxic because they inhibit protein synthesis and ricin toxin is considered a model of this class which includes, but is not limited to, ricins, abrins, nigrins, the mistletoe lectins and the viscumin toxins, ebulins, pulchellin, pharatoxin, hurin, and phasin toxins. Many, but not all, of these protein toxins are dimers made up of A and B protein subunits. Subunit A is the actual toxin, while subunit B is a lectin (carbohydrate-binding protein) that helps deliver the toxic subunit protein inside cells by binding to components on the cell surface or cell membrane and triggering uptake by cells. Once inside a cell, the subunit A protein of ribosome inactivating toxins like Ricin is able to selectively catalyze the cleavage of an N-glycosidic bond in the 28S ribosomal RNA that is a crucial part of eukaryotic ribosomes (en.wikipedia.org/wiki/ribosome), the organelles inside cells that make proteins, thus inhibiting protein synthesis and essentially shutting down the cell.

AB toxins may enter the body through many routes including via mucosal surfaces such as the gut, nose, lungs or may be administered transdermally or by injection. Research on the metabolism of AB toxins in animals has led to key insights in the uptake of proteins and other compounds into animal cells. For example, ricin toxin targets cells with galactose residues on their external surfaces. Research studies have identified at least five different biochemical uptake mechanisms. These studies have shown that ricin uses both dynamin-dependent and -independent routes of uptake into cells. Additionally, ricin has been observed to trigger endocytosis by interaction with the high mannose receptors based on its own mannose terminated glycans in addition to clathrin-dependent and -independent pathways. Clearly an important feature leading to the effectiveness of AB plant toxins in animals is the specialization of the A and B subunits of these proteins and the functional optimization of each subunit (A subunit: toxicity and B subunit: delivery) presumable thru evolution. Because of toxicity of AB toxins they have not been exploited systematically in drug discovery programs; this patent presents an invention which overcomes this drawback.

There are also other classes of lectins that do not specifically comprise AB toxins but possess lectin-mediated ability to bind to cell surface components and to direct uptake into cells and transcytosis across cells and to carry or deliver associated molecules. The best characterized lectins in this class typically have been identified from plants and include, but are not limited to, lectins such as wheat germ agglutinin, phytohemagglutin, Concanavalin A, the peanut and soybean lectins, and Jacalins.

BRIEF SUMMARY OF THE INVENTION

The present invention concerns materials and methods for delivering therapeutic proteins or other substances to the sites of disease manifestation in the body, including the brain and central nervous system (CNS), the skeletal system, the heart and pulmonary system, as well as other organs. Compounds of the invention comprise a therapeutic compound or agent operatively linked or fused to a plant lectin (such as the non-toxic B subunit of an AB toxin (referred to herein as PTB-lectin)). The therapeutic compound or agent is one which is useful or effective for treating or ameliorating a disease or disorder afflicting a person or animal. Methods of the invention comprise administering a therapeutically effective amount of a compound of the invention to a person or animal in need of treatment. In one embodiment, the method is used to treat an LD. In another embodiment, the method is used to treat any disease in which development of the disease is manifest in abnormal functions of the brain, CNS, or other organ of the body.

BRIEF DESCRIPTION OF THE DRAWINGS

FIG. 2A. Diagram of the fusion gene construct which encoded an N-terminal plant signal peptide (PSP; signal peptide modified from the potato patatin gene), the human IDUA coding region ($IDUA_{OPT}$; DNA synthesized using tobacco codon preferences), the RTB coding region (RTB), and a C-terminal hexa-histidine tag (6×HIS). FIG. 2B. Gel analyses of purification fractions from leaves of Nicotiana benthamiana expressing the construct in FIG. 2A. IDUA:RTB-containing leaf material was extracted in a pH7.5 Tris/NaCl buffer containing 20 mM galactose, and crude protein extracts were subjected to ammonium sulfate precipitation, and then further purified by lactose affinity and size exclusion chromatography. The IDUA:RTB containing fractions were size separated by SDS-polyacrylamide gel electrophoresis and analyzed by Western immunoblotting using anti-IDUA antibodies for detection (WB) and by silver-staining which detects all proteins in the fraction (SS). Location of the molecular weight size markers are indicated for each gel.

FIG. 3A. Images were analyzed based on total red pixels per image divided by number of cells (DAPI-stained nuclei). FIG. 3B. Relative lysosomal numbers were compared by defining red "regions of interest" using BD Pathway Bioimaging software.

BRIEF DESCRIPTION OF THE SEQUENCES

Figure 1:
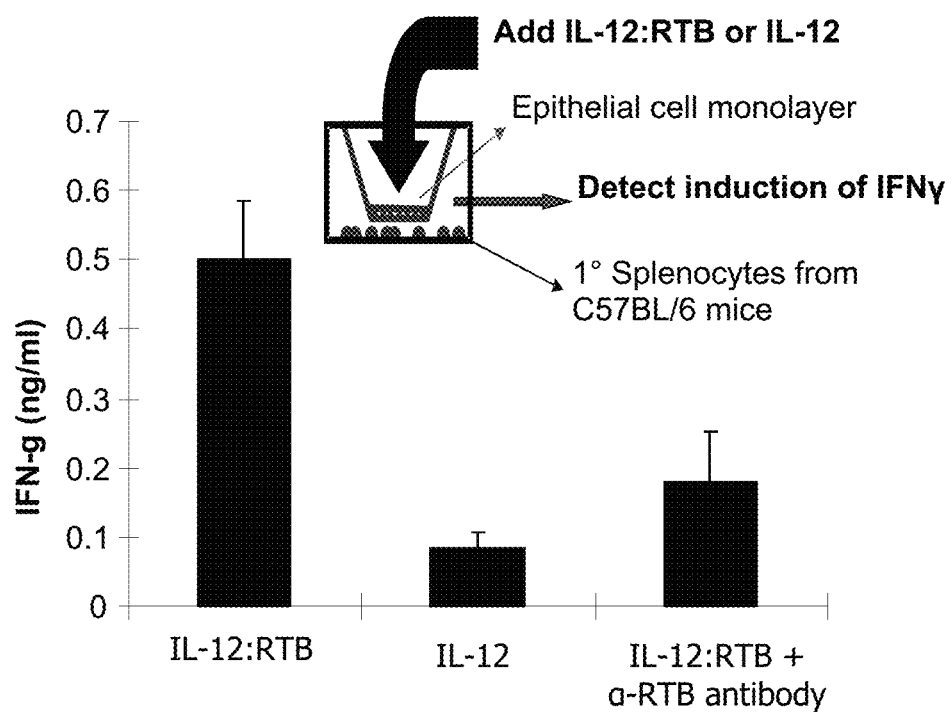
FIG. 1. RTB-mediated transcytosis. RTB carries fused interleukin-12 (IL-12) across a confluent HT29 cell layer and activates the production of interferon-γ in splenocytes below (Liu, Dolan, Cramer, unpublished data). Using an in vitro transcytosis model, mouse IL-12 alone or the PTB-lectin-mouse IL-12 genetic fusion product (RTB:IL-12), were added to the top of cells grown to tight confluence on an "insert" permeable membrane that had been placed over a cell layer of primary mouse splenocytes. The media of the lower splenocyte culture was subsequently analyzed for the presence of interferon-gamma (IFN-γ), the signature readout of IL-12 activity in splenocytes. RTB:IL-12, but not IL-12 alone, stimulated IFN-γ production. This stimulation was substantially blocked by addition of anti-RTB antibodies to the upper chamber indicating that the RTB lectin activity was fundamental in mediating transport across the epithelial layer for delivery to the cells below.

SEQ ID NO:1 is an amino acid sequence of a fusion protein of the invention comprising PoSP signal sequence, IDUA, RTB (truncated), and 6×His tag.

SEQ ID NO:2 is an amino acid sequence of a fusion protein of the invention comprising PoSP signal sequence, IDUA, NBB, and 6×His tag.

SEQ ID NO:3 is an amino acid sequence of a fusion protein of the invention comprising PoSP signal sequence, DsRed, NBB, and 6×His tag.

SEQ ID NO:4 is an amino acid sequence of a fusion protein of the invention comprising PoSP signal sequence, NBB, SGSH, and 6×His tag.

SEQ ID NO:5 is an amino acid sequence of a fusion protein of the invention comprising hSP, SGSH, RTB (truncated), and 6×His tag.

SEQ ID NO:6 is an amino acid sequence of a fusion protein of the invention comprising IDUA and RTB (truncated).

SEQ ID NO:7 is an amino acid sequence of a fusion protein of the invention comprising IDUA and NBB.

SEQ ID NO:8 is an amino acid sequence of a fusion protein of the invention comprising DsRed and NBB.

SEQ ID NO:9 is an amino acid sequence of a fusion protein of the invention comprising NBB and SGSH.

SEQ ID NO:10 is an amino acid sequence of a fusion protein of the invention comprising SGSH and RTB (truncated).

SEQ ID NO:11 is an amino acid sequence of a modified patatin signal sequence.

DETAILED DESCRIPTION OF THE INVENTION

The present invention concerns materials and methods for delivering therapeutic proteins or other substances, such as drugs, to the sites of disease manifestation in the body, including, but not limited to the brain and central nervous system (CNS), bone, lungs, and heart, eyes, ears, kidney, liver and spleen. In some embodiments, the system employs compounds comprising a plant lectin, such as the subunit B lectin proteins responsible for delivering toxin subunit A proteins to cells in the class of toxins known as AB protein exotoxins which utilize lectin binding sites on a targeted cell surface to gain entrance to cells via an endocytic pathway. AB toxins include the family of plant-made AB toxins (also called Toxalbumins) which include but are not limited to ricins, abrins, nigrins, the mistletoe lectins and the viscumin toxins, ebulins, pulchellin, pharatoxin, hurin, and phasin. These AB toxins are typically delivered to the cell via diverse endocytic pathways including the clathrin-dependent, clathrin-independent, and caveolae pathways. In one embodiment of the present invention, a therapeutic protein or other compound is fused or linked to the subunit B, or a fragment or variant thereof, as a substitution for the natural toxic subunit A component. In some embodiments, the subunit B lectin protein is from ricin. In specific embodiments, the ricin B subunit that is utilized is truncated by removal of about 1 to 10 amino acids at the N-terminus of the protein. In an exemplified embodiment, the ricin B subunit is truncated wherein the first six amino acids of the protein are removed. This fusion protein (or other compound) may be produced by construction of a fusion gene incorporating a nucleotide sequence encoding a plant lectin (such as the subunit B lectin) and a nucleotide sequence encoding the therapeutic protein, and introducing this new genetic fusion (fusion gene) into a protein expression system, expressing the fusion protein encoded by the fusion gene, and isolating the fused protein for use as a therapeutic drug. Alternatively, the fusion may be accomplished by direct chemical fusion or conjugation yielding fusion of the plant lectin (such as a subunit B protein) with the therapeutic agent. In one embodiment, the fusion protein comprises a linker or spacer sequence of amino acids between the plant lectin and the therapeutic protein or compound. Examples of linker or spacer sequences are well known in the art. Methods for preparing fusion genes and fusion protein are also well known in the art and have been described, for example, in U.S. Pat. Nos. 7,964,377; 7,867,972; 7,410,779; 7,011,972; 6,884,419; and 5,705,484. In an additional embodiment of the invention, inter- and intracellular trafficking dynamics are directed or modified to enhance effectiveness as managed by sequence or chemical modifications of the fusion product of the invention. These modifications may include, for example, glycans, amino acids, nucleotides, peptides, and methylation. In still another embodiment, fusion products of the invention are produced in a stable or transient transgenic plant expression system. In one embodiment, a method for preparing a fusion product of the invention comprises expressing a polynucleotide encoding the fusion product in a cell and isolating the expressed fusion product from the cell.

Plant lectins that are contemplated within the scope of the invention include, but are not limited to those B subunits from AB toxins such as ricins, abrins, nigrins, and mistletoe toxins, viscumin toxins, ebulins, pharatoxin, hurin, phasin, and pulchellin. They may also include lectins such as wheat germ agglutinin, peanut agglutinin, and tomato lectin that, while not part of the AB toxin class, are still capable of binding to animal cell surfaces and mediating endocytosis and transcytosis. Specific examples of plant lectins including their binding affinities and trafficking behavior are discussed further below. Therapeutic compounds and agents contemplated within the scope of -continued Type 2 Ribosome-Inactivating Proteins and Related Lectins:
Occurrence, Molecular Structure, and Specificity

| Species | Tissue | Structure[a] | Specificity | Sequence available[b] |
|---|---|---|---|---|
| Chimerolectins | | | | |
| Abrus precatorius | Seed | [P(34 + 32)] | Gal > GalNAc | Pr, Nu (Abrin) |
| | Seed | [P(33 + 29)]$_3$ | Gal | Pr (APA) |
| Adenia digitata | Root | [P(28 + 38)] | Gal > GalNAc | |
| Adenia volkensii | Root | [P(29 + 36)] | Gal | |
| Cinnamonum camphora | Seed | [P(30 + 33)]$_1$ | Unknown | |
| Eranthia hyemalius | Tuber | [P(30 + 32)] | GalNAc | |
| Ida hybrid | Bulb | [P(27 + 34)] | GalNAc | |
| Momordica charantia | Seed | [P(28 + 30)]$_1$ | Gal > GalNAc | |
| Phoradendron califomicum | Plant | [P(31 + 38)] | Gal | |
| Ricinus communis | Seed | [P(32 + 34)] | Gal > GalNAc | Pr, Nu (Ricin) |
| | Seed | [P(32 + 36)]$_2$ | Gal >> GalNAc | Pr, Nu (RCA) |
| Sambucus canadensis | Bark | I [P(32 + 35)]$_4$ | NANA | |
| Sambucus ebulus | Bark | I [P(32 + 37)]$_4$ | NANA | |
| | Leaf | [P(26 + 30)]$_2$ | GalNAc | |
| Sambucus nigra | Seed | Vs [P(26 + 32)]$_2$ | GalNAc > Gal | |
| | Bark | I [P(32 + 36)]$_4$ | NANA | Nu (SNA-I) |
| | Bark | I' [P(32 + 36)]$_2$ | NANA | Nu (SNA-I') |
| | Bark | V [P(26 + 32)]$_2$ | GalNAc > Gal | Nu (SNA-V) |
| | Fruit | If [P(32 + 35)]$_2$ | NANA | Nu |
| | Fruit | Vf [P(26 + 32)]$_2$ | GalNac > Gal | Nu |
| Sambucus racemosa | Bark | I [P(30 + 36)]$_4$ | NANA | |
| Sambucus sieboldiana | Bark | I [P(31 + 37)]$_4$ | NANA | Nu (SSA-I) |
| | Bark | [P(27 + 32)] | GalNAc > Gal | Nu (Sieboldin) |
| Viscum album | Plant | I [P(29 + 34)]$_{1-2}$ | Gal | |
| | Plant | II [P(29 + 34)] | Gal/GalNAc | |
| | Plant | III [P(25 + 30)] | GalNAc > Gal | |
| Type 2 RIP with inactive B chain | | | | |
| Sambucus nigra | Bark | [P(32 + 32)] | — | Nu (LRPSN) |

[a][PX] stands for protomer with a molecular mass of X kDa. [P(Y + Z)] indicates that the protomer is observed in two polypeptides of Y and Z kDa.
[b]Pr, protein sequence; Nu, nucleotide sequence. The abbreviation in brackets refers to the sequence name used in the dendrogram (FIG. 20).

As a further example of plant lectins contemplated herein, the table below exemplifies the large number of different lectins identified from the *Sambucus* species alone. This group includes nigrin B, the source on NBB.

Ribosome-inactivating proteins (RIPs) and lectins from *Sambucus* species. Adapted from Table 1 of Ferreras et al. (2011)

| Proteins | Species | Tissues |
|---|---|---|
| Type 1 RIPs | | |
| Ebulitins α, β and γ | S. ebulus | Leaves |
| Nigritins f1 and f2 | S. nigra | Fruits |
| Heterodimeric type 2 RIPs | | |
| Ebulin l | S. ebulus | Leaves |
| Ebulin f | S. ebulus | Fruits |
| Ebulins r1 and r2 | S. ebulus | Rhizome |
| Nigrin b, basic nigrin b, SNA I', SNLRPs | S. nigra | Bark |
| Nigrins l1 and l2 | S. nigra | Leaves |
| Nigrin f | S. nigra | Fruits |
| Nigrin s | S. nigra | Seeds |
| Sieboldin b | S. sieboldiana | Bark |
| Basic racemosin b | S. racemosa | Bark |
| Tetrameric type 2 RIPs | | |
| SEA | S. ebulus | Rhizome |
| SNA I | S. nigra | Bark |
| SNAIf | S. nigra | Fruits |
| SNAflu-I | S. nigra | Flowers |
| SSA | S. sieboldiana | Bark |
| SRA | S. racemosa | Bark |

-continued

Ribosome-inactivating proteins (RIPs) and lectins from *Sambucus* species. Adapted from Table 1 of Ferreras et al. (2011)

| Proteins | Species | Tissues |
|---|---|---|
| Monomeric lectins | | |
| SELlm | S. ebulus | Leaves |
| SEA II | S. ebulus | Rhizome |
| SNA II | S. nigra | Bark |
| SNAlm and SNAIVl | S. nigra | Leaves |
| SNA IV | S. nigra | Fruits |
| SNA III | S. nigra | Seeds |
| SSA-b-3 and SSA-b-4 | S. sieboldiana | Bark |
| SRAbm | S. racemosa | Bark |
| Homodimeric lectins | | |
| SELld | S. ebulus | Leaves |
| SELfd | S. ebulus | Fruits |
| SNAld | S. nigra | Leaves |

The subject invention also concerns polynucleotides that comprise nucleotide sequences encoding a fusion protein (or compound) of the invention. In one embodiment, the polynucleotides comprise nucleotide sequences that are optimized for expression in a particular expression system, e.g., a plant expression system, such as a tobacco plant. The subject invention also concerns the fusion polypeptides encoded by polynucleotides of the invention.

Any disease or disorder that can be treated or prevented using a therapeutic compound or agent is contemplated within the scope of the present invention. In one embodiment, the disease or disorder is one of the brain or CNS. Lysosomal diseases and (parenthetically) related enzymes and proteins associated with diseases that are contemplated within the scope of the invention include, but are not limited to, Activator Deficiency/GM2 Gangliosidosis (beta-hexosaminidase), Alpha-mannosidosis (alpha-D-mannosidase), Aspartylglucosaminuria (aspartylglucosaminidase), Cholesteryl ester storage disease (lysosomal acid lipase), Chronic Hexosaminidase A Deficiency (hexosaminidase A), Cystinosis (cystinosin), Danon disease (LAMP2), Fabry disease (alpha-galactosidase A), Farber disease (ceramidase), Fucosidosis (alpha-L-fucosidase), Galactosialidosis (cathepsin A), Gaucher Disease (Type I, Type II, Type III) (beta-glucocerebrosidase), GM1 gangliosidosis (Infantile, Late infantile/Juvenile, Adult/Chronic) (beta-galactosidase), I-Cell disease/Mucolipidosis II (GlcNAc-phosphotransferase), Infantile Free Sialic Acid Storage Disease/ISSD (sialin), Juvenile Hexosaminidase A Deficiency ((hexosaminidase A), Krabbe disease (Infantile Onset, Late Onset) (galactocerebrosidase), Metachromatic Leukodystrophy (arylsulfatase A), Mucopolysaccharidoses disorders [Pseudo-Hurler polydystrophy/Mucolipidosis IIIA (N-acetylglucosamine-1-phosphotransferase), MPSI Hurler Syndrome (alpha-L iduronidase), MPSI Scheie Syndrome (alpha-L iduronidase), MPS I Hurler-Scheie Syndrome (alpha-L iduronidase), MPS II Hunter syndrome (iduronate-2-sulfatase), Sanfilippo syndrome Type A/MPS III A (heparan N-sulfatase), Sanfilippo syndrome Type B/MPS III B (N-acetyl-alpha-D-glucosaminidase), Sanfilippo syndrome Type C/MPS III C (acetyl-CoA, alpha-glucosaminide acetyltransferase, Sanfilippo syndrome Type D/MPS III D (N-acetylglucosamine-G-sulfate-sulfatase), Morquio Type A/MPS IVA (N-acetylgalatosamine-6-sulfate-sulfatase), Morquio Type B/MPS IVB (β-galactosidase-1), MPS IX Hyaluronidase Deficiency (hyaluronidase), MPS VI Maroteaux-Lamy (arylsulfatase B), MPS VII Sly Syndrome (beta-glucuronidase), Mucolipidosis I/Sialidosis (alpha-N-acetyl neuraminidase), Mucolipidosis IIIC (N-acetylglucosamine-1-phosphotransferase), Mucolipidosis type IV (mucolipin1)], Multiple sulfatase deficiency (multiple sulfatase enzymes), Niemann-Pick Disease (Type A, Type B, Type C) (sphingomyelinase), Neuronal Ceroid Lipofuscinoses [(CLN6 disease—Atypical Late Infantile, Late Onset variant, Early Juvenile (ceroid-lipofuscinosis neuronal protein 6); Batten-Spielmeyer-Vogt/Juvenile NCL/CLN3 disease (battenin); Finnish Variant Late Infantile CLN5 (ceroid-lipofuscinosis neuronal protein 5); Jansky-Bielschowsky disease/Late infantile CLN2/TPP1 Disease (tripeptidyl peptidase 1); Kufs/Adult-onset NCL/CLN4 disease; Northern Epilepsy/variant late infantile CLN8 (ceroid-lipofuscinosis neuronal protein 8); Santavuori-Haltia/Infantile CLN1/PPT disease (palmitoyl-protein thioesterase 1); Beta-mannosidosis (beta-mannosidase)], Tangier disease (ATP-binding cassette transporter ABCA1), Pompe disease/Glycogen storage disease type II (acid maltase), Pycnodysostosis (cathepsin K), Sandhoff disease/Adult Onset/GM2 Gangliosidosis (beta-hexosaminidases A and B), Sandhoff disease/GM2 gangliosidosis—Infantile, Sandhoff disease/GM2 gangliosidosis—Juvenile (beta-hexosaminidases A and B), Schindler disease (alpha-N-acetylgalactosaminidas), Salla disease/Sialic Acid Storage Disease (sialin), Tay-Sachs/GM2 gangliosidosis (beta-hexosaminidase), and Wolman disease (lysosomal acid lipase), Sphingolipidosis, Hurmansky-Pudiak Syndrome (HPS1, HPS3, HPS4, HPS5, HPS6 and HPS7) Type 2-AP-3 complex subunit beta-1, Type 7-dysbindin), Chediak-Higashi Syndrome (lysosomal trafficking regulator protein), and Griscelli disease (Type 1: myosin-Va, Type 2: ras-related protein Rab-27A, Type 3: melanophilin).

Additional diseases (including related proteins) that may be therapeutically addressed by this invention include the neurodegenerative diseases which include but are not limited to Parkinson's, Alzheimer's, Huntington's, and Amyotrophic Lateral Sclerosis ALS (superoxide dismutase), Hereditary emphysema (α1-Antitrypsin), Oculocutaneus albinism (tyrosinase), Congenital sucrase-isomaltase deficiency (Sucrase-isomaltase), and Choroideremia (Rep1) Lowe's Oculoceribro-renal syndrome (PIP2-5-phosphatase). Many other genetic diseases are caused by deficiencies in specific proteins or enzymes leading to disease specific tissue and organ pathologies. ERT's or other protein replacement therapeutics may be of value for these diseases. PTB-lectins may facilitate protein delivery to critical organs, cells and subcellular organelles or compartments for these diseases as well. For example, genetic diseases affecting bone and connective tissues including, but are not limited to osteoporosis and osteogenesis imperfecta, may be treated by using this invention to deliver corrective proteins to bones, joints, and other connective tissues.

The enzymes or other proteins that can be used therapeutically in a fusion protein of the present invention can be identified by a person of ordinary skill in the art. For example, in treating MPS I disease, the therapeutic protein can provide iduronidase enzymatic activity. For treating Fabry disease, the therapeutic protein can provide a-galactosidase A enzymatic activity. Enzymes suitable for treating other LSDs are known in the art.

The present invention contemplates products in which the plant lectin is operatively associated with the therapeutic component by one of many methods known in the art. For example, genetic fusions between a plant lectin protein and a therapeutic protein can orient the lectin partner on either the C- or N-terminus of the therapeutic component. The coding regions can be linked precisely such that the last C-terminal residue of one protein is adjacent to the first N-terminal residue of the mature (i.e., without signal peptide sequences) second protein. Alternatively, additional amino acid residues can be inserted between the two proteins as a consequence of restriction enzyme sites used to facilitate cloning at the DNA level. Additionally, the fusions can be constructed to have amino acid linkers between the proteins to alter the physical spacing. These linkers can be short or long, flexible (e.g., the commonly used (Gly$_4$Ser)$_3$ 'flexi' linker) or rigid (e.g., containing spaced prolines), provide a cleavage domain (e.g., see Chen et al. (2010)), or provide cysteines to support disulfide bond formation. The plant lectins are glycoproteins and in nature are directed through the plant endomembrane system during protein synthesis and post-translational processing. For this reason, production of recombinant fusion proteins comprising a plant lectin and a therapeutic protein partner may require that a signal peptide be present on the N-terminus of the fusion product (either on the lectin or on the therapeutic protein depending on the orientation of the fusion construct) in order to direct the protein into the endoplasmic reticulum during synthesis. This signal peptide can be of plant or animal origin and is typically cleaved from the mature plant lectin or fusion protein product during synthesis and processing in the plant or other eukaryotic cell. In one embodiment, a modified patatin signal sequence (PoSP) is utilized: MASSATTKS-FLILFFMILATTSSTCAVD (SEQ ID NO:11) (see GenBank accession number CAA27588.1, version GI:21514 by Bevan et al. and referenced at "The structure and transcription start site of a major potato tuber protein gene" *Nucleic Acid Res.* 14 (11), 4625-4638 (1986)).

Compounds of the subject invention can also be prepared by producing the plant lectin and the therapeutic drug or protein separately and operatively linking them by a variety of chemical methods. Examples of such in vitro operative associations include conjugation, covalent binding, protein-protein interactions or the like (see, e.g., Lungwitz et al. (2005); Lovrinovic and Niemeyer (2005)). For example, N-hydroxysuccinimde (NHS)-derivatized small molecules and proteins can be attached to recombinant plant lectins by covalent interactions with primary amines (N-terminus and lysine residues). This chemistry can also be used with NHS-biotin to attach biotin molecules to the plant lectin supporting subsequent association with streptavidin (which binds strongly to biotin) and which itself can be modified to carry additional payload(s). In another example, hydrazine-derivatized small molecules or proteins can be covalently bound to oxidized glycans present on the N-linked glycans of the plant lectin. Proteins can also be operatively linked by bonding through intermolecular disulfide bond formation between a cysteine residue on the plant lectins and a cysteine residue on the selected therapeutic protein. It should be noted that the plant AB toxins typically have a single disulfide bond that forms between the A and B subunits. Recombinant production of plant B subunit lectins such as RTB and NBB yield a product with an 'unpaired' cysteine residue that is available for disulfide bonding with a "payload" protein. Alternatively, this cysteine (e.g., $Cys_4$ in RTB) can be eliminated in the recombinant plant lectin product by replacement with a different amino acid or elimination of the first 4-6 amino acids of the N-terminus to eliminate the potential for disulfide bonding with itself or other proteins.

Exemplified amino acid sequences of plant lectin fusion proteins of the present invention are provided (see SEQ ID NOs:1-10) and include genetic fusion wherein a) the plant lectin is either RTB (the B subunit of ricin) or NBB (the B subunit of nigrin B), b) the associated protein is either human a-L-iduronidase (IDUA), human sulfaminidase (SGSH), or DsRed fluorescent protein, c) the plant lectin comprises either the C-terminal or N-terminal partner of the fusion protein, d) the fusion protein comprises a precise fusion between partners adding no additional amino acids, e) the fusion protein includes at least one or two additional amino acids resulting from an added restriction site in cloning, and/or f) modifications are made at the C- or N-termini of one or both protein partners to add or eliminate a signal peptide, remove a cysteine residue, or add a C-terminal histidine tag. All fusion products are tested for functionality of both partners (e.g., plant lectin carbohydrate binding selectivity and enzyme activity or fluorescence of its fusion partner) and optimal activity of one or both partners can be affected by the fusion arrangement (N- versus C-terminal) and physical spacing. Development of effective dual function fusions between the plant lectin and the therapeutic protein can be readily accomplished using standard materials and methods known in the art by an ordinarily skilled artisan.

Additional information concerning IDUA, SGSH, DsRed, NBB, and RTB can be found at:

IDUA: See GenBank accession number pbd/4JXP_A version GI:480312357 by Bie et al. and referenced at "Crystal structure analysis of human alpha-L-iduroni two crystal forms" Unpublished, and see GenBank accession number AAA81589.1, version GI:184559 by Scott et al. and referenced at "Human alpha-L-iduronidase: cDNA isolation and expression" *Proc. Natl. Acad. Sci. U.S.A.* 88 (21), 9695-9699 (1991).

DsRed: See GenBank accession number pbd/1G7K (Chain A, B, C, D) versions GI:12084491, 12084492, 12084493, 12084494 by Matz et al. and referenced at "Fluorescent proteins from nonbioluminescent Anthozoa species" *Nat. Biotechnol.* 17(10), 969-973 (1999).

NBB: See GenBank accession number P33183.2, version GI:17433713 (containing subunits A and B) by Van Damme et al. and referenced at "Characterization and molecular cloning of *Sambucus nigra* agglutinin V (nigrin b), a GalNAc-specific type-2 ribosome-inactivating protein from the bark of elderberry (*Sambucus nigra*)" *Eur. J. Biochem.* 237 (2), 505-513 (1996). PDB ID: 3CA3 (for B subunit) by Maveyraud et al. and referenced at "Structural basis for sugar recognition, including the to carcinoma antigen, by the lectin sna-ii from *sambucus nigra" Proteins* 75 p. 89 (2009).

SGSH: See GenBank accession number NP 000190.1, version GI:4506919 by Van de Kamp et al. and referenced at "Genetic heterogeneity and clinical variability in the Sanfilippo syndrome (type A, B, and C)" *Clin. Genet.* 20 (2), 152-160 (1981).

RTB: See GenBank accession number pbd/2AAI/B, version GI:494727 (containing subunits A and B) by Montfort et al. and referenced at "The three-dimensional structure of ricin at 2.8A" *J. Biol Chem.* 262 (11), 5398-5403 (1987).

In vivo administration of the subject compounds, polynucleotides and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, transdermal, vaginal, and parenteral routes of administration. As used herein, the term parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art. In one embodiment, a polynucleotide encoding a therapeutic fusion product of the invention is stably incorporated into the genome of a person of animal in need of treatment. Methods for providing gene therapy are well known in the art. In one embodiment, a polynucleotide is provided in an expression construct and encodes an amino acid sequence of any of SEQ ID NOs:1-10.

The compounds of the subject invention, and compositions comprising them, can also be administered utilizing liposome and nano-technology, slow release capsules, implantable pumps, and biodegradable containers, and orally or intestinally administered intact plant cells expressing the therapeutic product. These delivery methods can, advantageously, provide a uniform dosage over an extended period of time.

Compounds of the subject invention can be formulated according to known methods for preparing physiologically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds and agents of the invention, and compositions thereof, may be locally administered at one or more anatomical sites, optionally in combination with a pharmaceutically acceptable carrier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and agents, and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound and/or agent of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a composition comprising a compound and/or agent and/or polynucleotide of the invention in one or more containers. Kits of the invention can optionally include pharmaceutically acceptable carriers and/or diluents. In one embodiment, a kit of the invention includes one or more other components, adjuncts, or adjuvants as described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent and/or polynucleotide of the invention is provided in the kit as a solid, such as a tablet, pill, or powder form. In another embodiment, a compound and/or agent and/or polynucleotide of the invention is provided in the kit as a liquid or solution. In one embodiment, the kit comprises an ampoule or syringe containing a compound and/or agent of the invention in liquid or solution form.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cultured cells or tissues of such human and non-human species.

The subject invention also concerns bacterial cells, and animals, animal tissue, and animal cells, and plants, plant tissue, and plant cells of the invention that comprise or express a polynucleotide or the protein encoded by the polynucleotide of the invention, or a fragment or variant thereof. Plant tissue includes, but is not limited to, seed, scion, and rootstock. Plants within the scope of the present invention include monocotyledonous plants, such as, for example, rice, wheat, barley, oats, rye, sorghum, maize, sugarcane, pineapple, onion, bananas, coconut, lilies, turfgrasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. Herb plants containing a polynucleotide of the invention are also contemplated within the scope of the invention. Herb plants include parsley, sage, rosemary, thyme, and the like. In one embodiment, a plant, plant tissue, or plant cell is a transgenic plant, plant tissue, or plant cell. In another embodiment, a plant, plant tissue, or plant cell is one that has been obtained through a breeding program.

Polynucleotides encoding a fusion product of the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation. In one embodiment, an expression construct comprises a polynucleotide encoding an amino acid sequence of any of SEQ ID NOs:1-10.

An expression construct of the invention can comprise a promoter sequence operably linked to a polynucleotide sequence of the invention, for example a sequence encoding a fusion polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2002), and Hwang et al. (2002). Root-specific promoters, such as any of the promoter sequences described in U.S. Pat. No. 6,455,760 or U.S. Pat. No. 6,696,623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode polypeptides and enzymes of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, polypeptides and enzymes of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a wild type polypeptide of the invention are also encompassed within the scope of the invention.

Substitution of amino acids other than those specifically exemplified or naturally present in a wild type polypeptide or enzyme of the invention are also contemplated within the scope of the present invention. For example, non-natural amino acids can be substituted for the amino acids of a polypeptide, so long as the polypeptide having the substituted amino acids retains substantially the same biological or functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type polypeptide or enzyme of the present invention are also encompassed within the scope of the invention.

Amino acids can be generally categorized in the following classes: non-polar, uncharged polar, basic, and acidic. Conservative substitutions whereby a polypeptide or enzyme of the present invention having an amino acid of one class is replaced with another amino acid of the same class fall within the scope of the subject invention so long as the polypeptide having the substitution still retains substantially the same biological or functional activity (e.g., enzymatic) as the polypeptide that does not have the substitution. Polynucleotides encoding a polypeptide or enzyme having one or more amino acid substitutions in the sequence are contemplated within the scope of the present invention. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a polypeptide or enzyme of the present invention can be generated as described herein and tested for the presence of biological or enzymatic function using standard techniques known in the art. Thus, an ordinarily skilled artisan can readily prepare and test fragments and variants of a polypeptide or enzyme of the invention and determine whether the fragment or variant retains functional or biological activity (e.g., enzymatic activity) relative to full-length or a non-variant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and)(BLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and)(BLAST) can be used. See NCBI/NIH website.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a polynucleotide or gene are known in the art and include, for example, *Agrobacterium* infection, transient uptake and gene expression in plant seedlings, biolistic methods, electroporation, calcium chloride treatment, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention. In one embodiment, the cell is transformed with a polynucleotide sequence comprising a sequence encoding the amino acid sequence shown in SEQ ID NOs:1-10, or a biologically active fragment or variant thereof.

The subject invention also concerns cells transformed with a polynucleotide of the present invention encoding a polypeptide or enzyme of the invention. In one embodiment, the cell is transformed with a polynucleotide sequence comprising a sequence encoding the amino acid sequence shown in SEQ ID NOs:1-10, or a biologically active fragment or variant thereof. In one embodiment, the polynucleotide sequence of the invention is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. Animal cells include human cells, mammalian cells, avian cells, and insect cells. Mammalian cells include, but are not limited to, COS, 3T3, and CHO cells.

Single letter amino acid abbreviations are defined in Table 2.

TABLE 2

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

PTB-lectins can carry and deliver fused payloads (genetically fused proteins or conjugated small molecules) into mammalian epithelial cells (e.g., HT29 human gut epithelial cells, HeLa cells, A549 lung epithelial cells). Genetic fusions of RTB (the lectin subunit B of ricin) or NBB (the lectin B subunit of nigrin B) with Green Fluorescent Protein or Red Fluorescent Protein (DsRed) were produced and purified. The lectin:fluorescent fusion proteins were then incubated with cultured cells at 0-4° C. to allow binding to the cell surface. Cells were then washed and incubated at 37° C. to initiate uptake into the cultured mammalian cells. The fluorescently tagged RTB and NBB was observed to bind to the cell surface at time zero and to move to internal punctuate structures by 30 to 60 minutes indicative of endosomal/lysosomal compartments. In contrast, incubation of cells with Green Fluorescent Protein or Red Fluorescent Protein that lacked the PTB-lectin did not bind to cells or transit to internal compartments indicating that the PTB-lectin was responsible for binding and uptake. Likewise, RTB that was labeled by conjugation with fluors (e.g., fluorescein; DyLight), or conjugation with biotin and then subsequent assembly with labeled strepavidin, also bound to the surface of mammalian endothelial cells and was transported to internal endosomal/lysosomal compartments based on fluorescent punctate structures observed at 30, 60, and 120 minutes incubation at 37° C. Furthermore, uptake into endosomal/lysosomal compartments was further documented by co-localization of RTB or NBB fusions or conjugates with lysosomal markers (e.g., Lysotracker-Red or Lysotracker-Green) or antibodies directed against the EEA early endosome marker.

Example 2

PTB-lectin carries fused proteins across confluent cell layers demonstrating transcytosis (FIG. 1). In other studies, we produced RTB fusions with the mouse cytokine interleukin-12 (IL-12). IL-12 triggers induction of interferon-γ (IFN-γ) in splenocytes but not epithelial cells. To demonstrate transcytosis, a confluent monolayer of HT29 cells was developed and placed as an insert over primary mouse splenocytes. IL-12:RTB, but not IL-12 alone, triggered IFN-g induction. Addition of anti-RTB neutralizing antibody blocked this induction (Liu, Dolan, Cramer, unpublished data).

Example 3

Plant-based production of recombinant PTB-lectin—human lysosomal fusion proteins yields proteins that simultaneously display selective lectin binding activity and lysosomal enzyme activity. In order to demonstrate that PTB-lectins successfully deliver lysosomal ERT (enzyme replacement therapy) enzymes to the cells and organelles that are critical targets for ameliorating symptoms of lysosomal diseases, we utilized several model ERTs including human α-L-iduronidase (IDUA) and the human sulfaminidase, N-sulfoglucosamine sulfohydrolase (SGSH). Gene constructs were developed that fused the coding region of the plant lectins RTB or NBB to the coding regions of the human lysosomal enzymes. Typically, the fusion partners were tested in both orientations (e.g., NBB:IDUA and IDUA:NBB). The genes encoded a plant signal peptide (the signal peptide from the potato patatin gene) to ensure that the recombinant product was targeted to the endoplasmic reticulum for addition of N-linked glycans. These genes were introduced into plant expression/transfection vectors (derivatives of pBIB-Kan; Becker (1990) and expressed in *Nicotiana benthamiana* leaves using a transient *Agrobacterium*-mediated expression system as described (Medrano et al. (2009)).

Figure 2A:
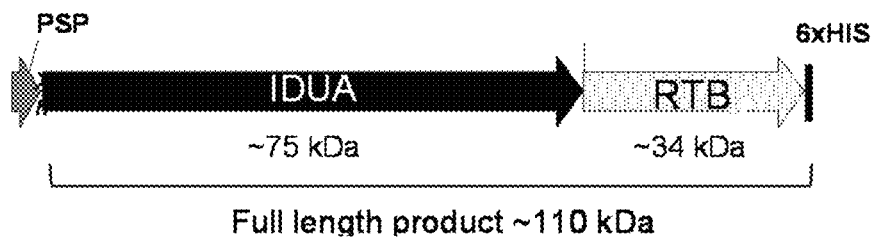
FIGS. 2A and 2B. Gene structure and purification of the PTB-lectin-lysosomal fusion product, IDUA:RTB.
Figure 2B:
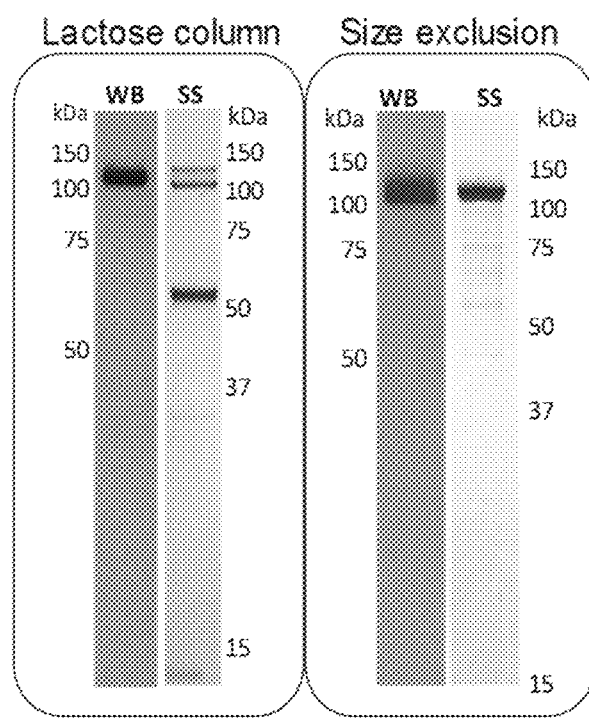

Gene constructs for NBB:IDUA, IDUA:NBB and IDUA:RTB were developed and expressed in *N. benthamiana*. In all cases, plants produced a protein of the expected molecular size (~110 kDa) product that cross-reacted with anti-IDUA specific antibodies on Western immunoblots (for example see FIG. 2). IDUA-specific enzyme activity was demonstrated for these plant-derived PTB-lectin-IDUA fusions using a fluorometric assay with sodium-4-methylumbelliferyl-α-L-iduronide (4-MUI) as substrate. Thus, fusion with the PTB-lectins did not interfere with IDUA enzymatic activity. Furthermore, results using a dual-activity assay involving RTB binding of plant-made products to immobilized asialofetuin (glycoprotein with high affinity for RTB) and detection/quantification of the lectin-bound IDUA activity using the standard 4-MUI enzymatic assay also showed that IDUA:RTB and retained both lectin-specificity and human enzyme activity.

Similarly, PTB-lection fusion constructs with human lysosomal sulfaminidase SGSH were developed in both orientations (i.e., with the human enzyme as either the C- or N-terminal partner) with both NBB and RTB. These constructs were expressed in *N. benthamiana*. To characterize the plant-synthesized products containing SGSH, SGSH-specific enzyme activity can be demonstrated using a fluorometric assay with 4-methylumbelliferyl-α-D-N-sulfoglucosaminide as substrate (e.g., Esposito et al. (2000)).

Example 4

PTB-lectin:lysosomal enzyme fusions correct substrate accumulation in LD cells. To demonstrate that PTB-lectins delivery active ERT enzymes to the cellular site of disease substrate, we produced IDUA:RTB, and IDUA:NBB in *N. benthamiana* and used the product to treat cultured fibroblasts from Hurler and Hurler/Scheie patients (patients with IDUA deficiency). The recombinant proteins were purified by a combination of ammonium sulfate precipitation, affinity chromatography, and size exclusion chromatography. The affinity chromatography process utilized lactose resin for RTB-containing products and N-acetyl-galactosamine resin for NBB-containing products. The ability of PTB-lectin:IDUA fusions to correct the lysosomal disease phenotype in Hurler and Hurler/Scheie cells was demonstrated based on reduction of lysosomal size and number. Because Hurler and Hurler Scheie patients cannot effectively clear cells of the glucosaminoglycan (GAG; the disease substrate) macromolecule, a characteristic cellular disease phenotype is enlarged lysosomes, the intracellular site of GAG accumulation. We therefore tested the ability of PTB-lectin fusions with IDUA to reduce the lysosomal volume per cell of diseased fibroblasts to those observed in normal fibroblasts. Untreated normal fibroblasts (NIH Cell Repository; Coriell #GM00010), Hurler fibroblasts (Coriell #01391) and Hurler/Scheie fibroblasts (Coriell #GM00963) were used as controls to set "normal" and "disease" levels. Commercially available animal-cell-derived recombinant human IDUA (rhIDUA, e.g. from R&D Systems), which includes mannose-6-phosphate-modified glycans to facilitate cell uptake, was also included as a positive control.

Figure 3A:
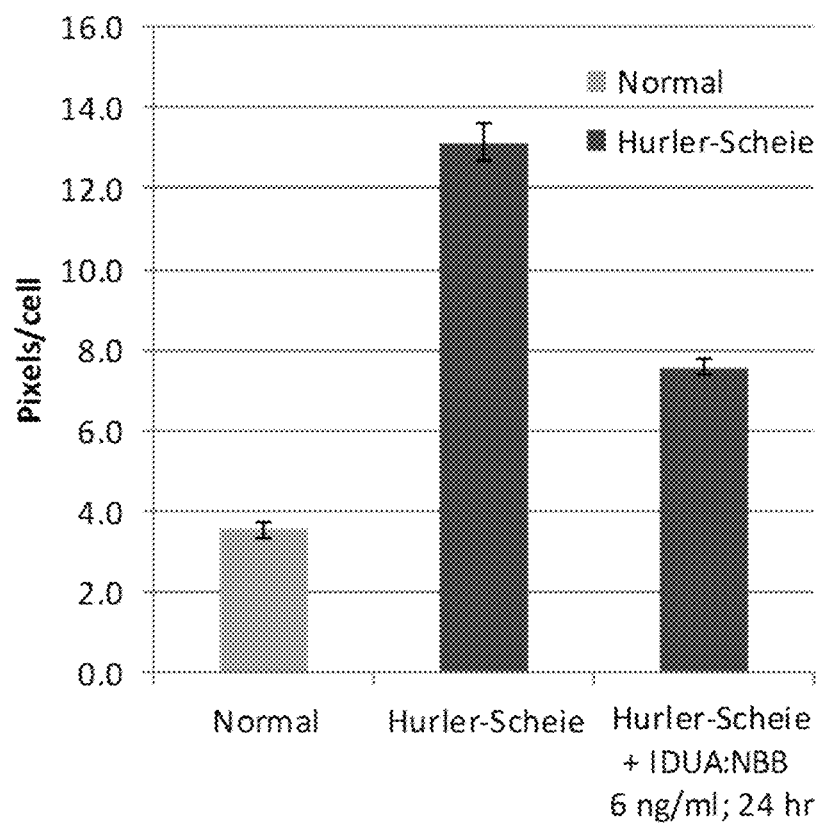
FIGS. 3A and 3B. Correction of lysosomal disease phenotype of Hurler/Scheie fibroblasts by treatment with IDUA:NBB as an example of PTB-lectin-mediated delivery of active lysosomal enzyme into cells and into the site of disease substrate accumulation leading to a reduction in lysosomal size. Normal and Hurler/Scheie fibroblasts were grown in multiple wells of 96-well plates (normal: 10 wells; Hurler/Scheie: 16 wells). IDUA:NBB was added to half of the wells (8) containing Hurler/Scheie cells at a concentration of 6 ng/ml and the plate was further incubated at 37° C. After 24 hr incubation, cells were stained with Lysotracker-Red (30 min), fixed and then nuclei were stained with DAPI blue. Cells were then imaged by confocal microscopy using a BD Pathway 855 Bioimaging System at 20× magnification with uniform settings that captured 4 images per well (each with average of ~200 cell).
Figure 3B:
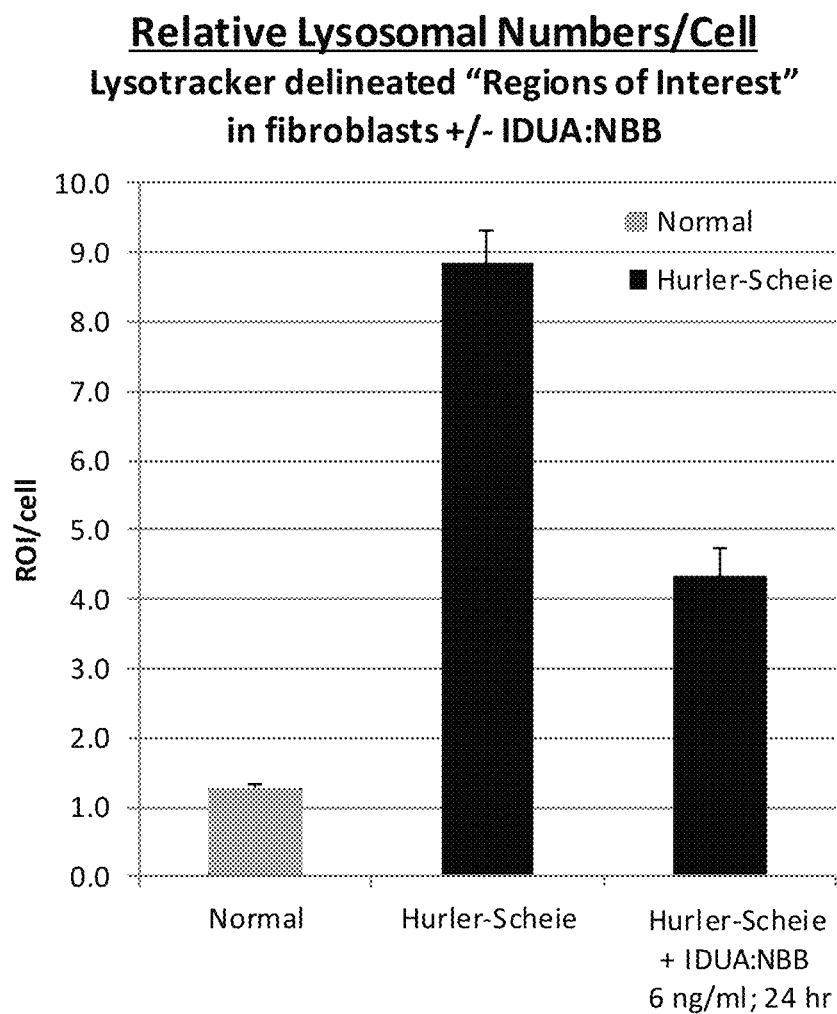

For these analyses, Normal and Hurler/Scheie fibroblasts were plated in a 96 well plate format. To assess correction of lysosomal phenotype, Hurler/Sheie fibroblasts were incubated for 20-24 hours with IDUA:NBB, IDUA:RTB or rhIDUA. Following incubation, lysosomes were detected using LYSOTRACKER red (Invitrogen), cells were fixed and nuclei were stained using DAPI blue (Invitrogen) to facilitate cell count per image. The BD Pathway 855 BioImaging System was used to collect 4×4 montage images per well using confocal image capture at 20× magnification. Fluorescent measurement analyses and cell counts were performed using the same segmentation parameters in all images. Lysosomal area was defined as the total area in pixels of red fluorescent signal per cell as defined by number of DAPI-stained nuclei) in each well. The lysosomal area/cell and lysosomal number/cell were significantly different between normal and Hurler/Scheie fibroblasts using this assay system. Both IDUA:NBB and IDUA:RTB reduced the lysosomal area and lysosomal number per Hurler/Scheie fibroblast to the levels observed in Normal fibroblasts (see representative IDUA:NBB data in FIG. 3).

The PTB-lectin technology can be used to deliver other lysosomal replacement enzymes such as the human SGSH acid sulfaminidase for treatment of Mucopolysaccharidosis IIIA (Sanfilippo A Disease). In order to demonstrate that PTB-lectin fusions with human SGSH correct cellular disease phenotypes, the PRT-lectin:SGSH fusion proteins are tested on primary cell cultures from Sanfilippo A patients (Coriell #GM01881) and mouse sgsh$^{-/-}$ knockout mice. Primary human fibroblasts from normal individuals and Sanfilippo A patients are cultured to near-confluency in 96-well plates and incubated for 48 h with purified PRT-lectin: SGSH fusions. Harvested cells are analyzed for reduction of sulfated GAG substrate levels and lysosomal area following treatment with PRT-lectin: SGSH fusions. Similar uptake and substrate correction experiments are performed using PRT-lectin:SGSH fusions administered to cultured sgsh$^{-/-}$ mouse MEFs, macrophages, and neurospheres. The elevated GAG levels present in Sanfilippo A human and mouse cells are expected to be reduced to normal levels following treatment with PRT-lectin: SGSH fusions indicating delivery of active and corrective enzyme to the site of disease substrate accumulation.

Example 5

Figure 4:
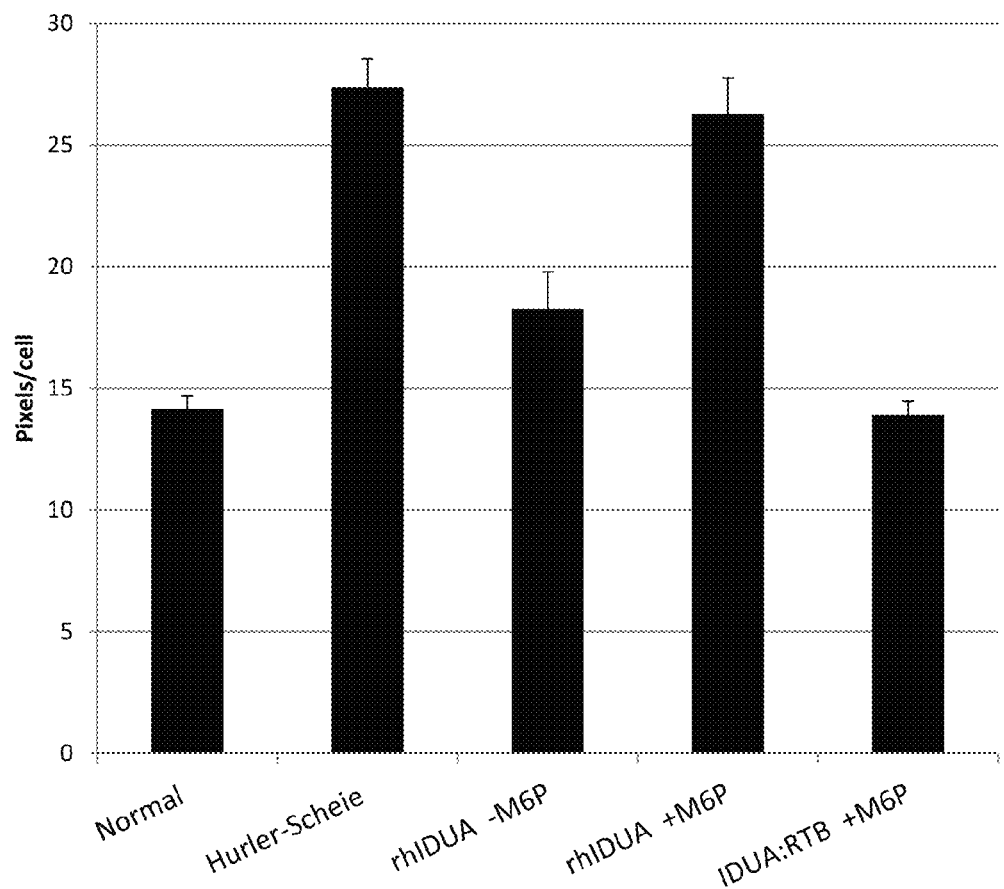
FIG. 4. PTB-lectins deliver associated lysosomal enzymes by mechanisms that are independent of the mannose-6-phosphate (M6P) receptor. Hurler/Scheie fibroblasts were incubated with (+M6P) or without (−M6P) inhibitory levels of mannose-6-phosphate (3 mm M6P sodium salt) for 2 hours prior to addition of 40 ng/ml IDUA equivalents as either a) plant-made IDUA:RTB or b) commercial human iduronidase (rhIDUA) synthesized in mammalian cells and containing M6P-modified glycans. After 24 hr incubation, cells were stained with Lysotracker-Red and DAPI and analyzed as described in FIG. 3. IDUA:RTB, but not rhIDUA, corrected the enlarged lysosomal phenotype of Hurler/Scheie cells in the presence of M6P indicating that RTB-mediated delivery functioned via M6P receptor-independent pathways.

PTB-lectin:lysosomal enzyme fusions correct substrate accumulation in LD disease cells by mechanisms that are independent of the mannose-6-phosphate receptor (M6PR). To demonstrate that PTB-lectins carry associated lysosomal enzymes into cells and lysosomes by mechanisms that differ from the current FDA-approved ERTs for Hurler and Hurler/Scheie Syndromes (mucopolysaccharidosis I) which uses the M6P receptor to deliver ERT into cells, we assayed Hurler/Scheie fibroblasts for disease phenotype correction in the presence of M6PR competitive inhibitors. To block the M6P receptor, Hurler/Scheie fibroblasts were incubated with 3 or 4 mM M6P (D-mannose-6-phosphate sodium salt) for 2 hours prior to the addition of IDUA:RTB or animal-cell derived rhIDUA. After 24 hr further incubation at 37° C., the cells were harvested and lysosomal area/cell and lysosome number/cell were determined by high-through-put confocal bioimage analyses following staining with Lysotracker-red and DAPI blue (see Example 4). Hurler cells treated with IDUA:RTB in the presence of M6P showed full correction of the lysosomal disease phenotype to those observed in Normal cells or in Hurler/Scheie cells treated in the absence of M6P (FIG. 4). In contrast, Hurler/Scheie cells treated with animal-cell-derived rhIDUA in the presence of M6P showed no correction of GAG levels, lysosomal area/cell or lysosome number/cell indicating that the levels used were fully inhibitory for cell uptake based on the M6P receptor. Our data confirmed that IDUA delivery and efficacy of the PTB-lectin fusions was M6PR-independent.

In addition, GAG levels and lysosomal area of Hurler/Scheie cells treated with IDUA:NBB in the presence of inhibitory levels of M6P or mannan are corrected to normal levels. Likewise, sulfated GAG levels and lysosomal area of SanfilippoA fibroblasts (Coriell #GM01881) treated with RTB:SGSH or SGSH:RTB in the presence of inhibitory levels of M6P or mannan are corrected to normal levels.

Example 6

PTB-lectins can deliver associated payload (genetically fused protein or conjugated compound) into cells, tissue and organs important in human disease pathology. PTB-lectins genetically fused with fluorescent marker proteins (e.g., GFP green fluorescent protein and the DsRed red fluorescent protein) or fluorescently labeled by conjugation (e.g., with fluorescein or Dylight) have been used to demonstrate delivery into cells and tissues that are associated with disease including lysosomal diseases. As detailed further below, normal and disease cells or tissues were treated by the addition of purified PTB-lectin proteins, incubated at 37° C. for various times (typically 0-24 hrs), and cell surface binding and uptake into intracellular compartments was monitored by fluorescence and/or confocal microscopy. Cells were often counter-stained with DAPI (blue) to delineate nuclei and organelle-selective compounds such as Lysotracker.

To demonstrate uptake of PTB-lectin and PTB-lectin fusion proteins into key cells of the central nervous system, primary neurosphere cultures were established from brain tissue of normal mice (as described in Tessitore et al. (2004)), treated with 1 µg/ml lectin equivalent of either a) RTB:GFP and b) DsRed:NBB and incubated overnight, and then stained for 30 minutes with Lysotracker-red or Lysotracker-green, respectively, prior to microscopic imaging. Both RTB:GFP and DsRed:NBB were detected intracellularly in punctate structures indicative of endosomal/lysosomal compartment and the majority co-localized with Lysotraker. All cells showed fusion protein uptake indicating that PTB-lectins mediate uptake into neurons and astrocytes of the brain. In other experiments, RTB:GFP and Dylight-labeled RTB were added to primary bovine brain microvessel endothelial cells that had been grown in vitro to tight confluency as a model of the blood brain barrier (BBB; methods as described in Bachmeier et al. (2006)). Both RTB:GFP and RTB$^{Dylight}$ showed efficient binding to brain endothelial cells and uptake into the endomembrane system at 30 and 60 minutes post-incubation. Based on this high level of RTB:GFP endocytosis into the brain endothelial layer that forms the blood brain barrier and documented RTB transcytosis in other cell types (e.g., see Example 2), it is expected that RTB- and NBB-fusions effectively carry associated proteins or drugs across the blood brain barrier and into neurons and astrocytes of the brain in both in vitro BBB models and in vivo. Likewise, it is expected that PTB-lectins effectively carry associated proteins or drugs across the analogous blood ocular barrier for delivery of payloads to disease cells of the eye.

To demonstrate uptake of PTB-lectin and PTB-lectin fusion proteins into key cells of the respiratory system, sections of metabolically active human lung sections were treated with RTB:GFP. These sections were developed by gently filling the airspace of lungs that were maintained on ice since harvest with low-melting-point agarose and then culturing excised tissue sections that encompassed airways and surrounding tissues. These tissues were able to mediate chemically-induced constriction and relaxation of airways indicating integrity of the tissue. After 4 hours incubation with RTB:GFP, tissues analyzed by confocal microscopy revealed uptake of RTB:GFP into intracellular compartments of aveolar epithelial cells, macrophages, and lung cartilage tissues and chondrocytes. Uptake was further confirmed in primary cell cultures of airway epithelial and smooth muscle cells from this human lung. Aveolar epithelial cells, analyzed at 30 to 120 min after RTB:GFP addition, showed efficient uptake into the endosomal/lysosomal compartments. Differentiating airway smooth muscle cells showed strong RTB:GFP localization to the sarcoplasmic reticulum.

The PTB-lectin technology could also be used to deliver associated proteins into key cells of the skeletal system. As mentioned above, RTB:GFP was efficiently taken up by the connective tissues of the human lung (cartilage; chondrocytes), macrophages (differentiated monocyte produced in bone marrow), and skin fibroblasts (of skeletal system lineage). Likewise, it is expected that PTB-lectins effectively carry associated proteins or drugs into osteoblasts and other key bone cells. To document this in an in vitro model of osteogenesis, fluorescently tagged PTB-lectins (e.g., RTB:GFP, DsRed:NBB) are added to cultures displaying osteogenic "bone nodules" and the uptake and subcellular location determined by confocal microscopy. In these systems which are well known in the field (e.g., Malaval et al. (1994); Gaddy-Kurten et al. (2002); Jørgensen et al. (2004); Lazarenko et al. (2006)), bone progenitor cells that have been cultured from rat, mouse, human bone marrow, or other sources multiply and differentiate to form nodules that contain differentiated osteoblasts, fibroblasts, adipocytes, and monocytes.

Example 7

PTB-lectins can deliver genetically fused human enzymes or therapeutic proteins into cells, tissue and organs important in human disease pathology. PTB-lectins genetically fused with human lysosomal enzymes such as IDUA and SGSH, can be used to demonstrate correction of cellular disease phenotype in cells and tissues strongly linked with disease pathology. For example, for Hurler (IDUA deficiency) and Sanfilippo A (SGSH deficiency) lysosomal diseases, disease impacts on the central nervous system can be devastating. To provide an in vitro assessment of PTB-lectin-mediated delivery of corrective enzyme to key cells of the CNS, neurospheres cultures are established from knockout mice for each disease. It is known that cells of neurospheres cultured from the mouse knockout models for lysosomal diseases having significant CNS involvement (e.g., see Tessitore et al. (2004)) show a distinctive phenotype including extensive vacuolization due to disease substrate accumulation in lysosome of the neurons and astrocytes. Neurosphere cultures established from sgsh$^{-/-}$ mice are treated with various concentrations of RTB:SGSH, SGSH:RTB, NBB:SGSH, or SGSH:NBB for 24 and 48 hours. Following incubation, treated and untreated cells are analyzed by confocal microscopy following staining with antibodies to accumulated disease substrate and/or Lysotracker and DAPI to visualize reduction in disease substrate and lysosomal volume. Use of neuron and astrocyte selective antibodies delineates disease phenotype correction in each cell type. Similarly, neurospheres cultures established from idua$^{-/-}$ mice are used to document correction of CNS pathologies at the cell level using PTB-lectin:IDUA fusions.

Likewise, for diseases where bone impairment represents a significant aspect of disease pathology, in vitro osteogenesis models (see Example 6) are used to document corrective PTB-lectin-mediated delivery of associated ERT enzymes.

Example 8

PTB-Lectins can Deliver Fused Active Lysosomal Enzymes to Animal Brains and Across the Blood Brain Barrier.

IDUA:RTB at several concentrations are administered into Balb/C mice by injection into a tail vein, the carotid artery, or the heart (left ventricle). Mice are euthanized at various times after injection (1, 2, and 4 hours) and saline perfused to remove fusion protein that remains in the plasma. Brains are removed with one half used for homogenization to assay directly for lectin:enzyme activity and the other half is used for analysis by fluorescence activated cell sorting (FACS) and/or flow cytometry. For direct enzyme assay, tissue is homogenized and used for dual-activity IDUA enzyme assays as described. This assay first captures lectin-active proteins based on binding to asialofetuin glycoprotein and thus detects only IDUA:RTB activity and not endogenous IDUA. Brain levels in animals treated with saline (mock) and IDUA:RTB are compared to show that IDUA activity is significantly higher in brains of animals receiving IDUA:RTB treatment. To demonstrate that RTB delivers IDUA across the BBB, treated brain tissue is dissociated and the resulting single cell suspension is reacted with cell-type specific surface antibodies for neurons and glial cells (Panchision et al. (2007); Yuan et al. (2011)) and subjected to FACS to provide selectively enriched populations of neuronal and glial cells. The enriched fractions are then analyzed for IDUA activity using the dual activity assay descripted above. In other experiments, brain cells from untreated or IDUA:RTB-treated mice are treated with neuron-selective surface antibodies and then permeabilized and incubated with anti-RTB antibodies and analyzed by flow cytometry. Similarly, untreated and treated brains cell can be differentially labeled with glial surface antibodies and anti-RTB antibodies and subjected to flow cytometry analyses. These analyses document the presence of the PTB-lectins within neurons and/or glial cells demonstrating transit across the BBB.

Example 9

RTB:Lysosomal Enzyme Fusions Deliver Active Enzyme to CNS Tissue in Knock-Out Mouse Models As an example to show that PTB-lectins deliver "corrective" doses of ERT in vivo, idua$^{-/-}$ mice (mouse model of Hurler syndrome including CNS pathology; Ohmi et al. (2003)) are treated with IDUA:RTB. To establish effective test doses and determine short-term biodistribution, idua$^{-/-}$ mice are given a single administration by tail-vein injection at varying doses ranging from 0.06 to 6.0 mg IDUA equivalent/kg body weight. Mice are euthanized at 1 hour or 4 hours post injection, bled, and perfused with saline. The drug is quantified on the basis of IDUA catalytic activity in key organs (e.g., liver, kidney, spleen, heart, cerebrum, and cerebellum) and in plasma to assess clearance from the circulation.

Disease correcting efficacy of IDUA:RTB is tested in idua$^{-/-}$ knockout mice by analyzing disease progression and impact on organ-specific pathologies following repeated administrations of IDUA:RTB for a 4 to 8 week period. idua$^{-/-}$ mice are treated weekly by intravenous injection.

Normal mice (idua$^{+/+}$ or idua$^{+/-}$) and untreated idua$^{-/-}$ mice are analyzed in parallel with IDUA:RTB-treated mice. Mice are photographed and analyzed for weight, urine GAG levels, and cognitive behavior (swimming T-maze) at onset and weekly starting at the initiation of treatment. idua$^{-/-}$ mice treated weekly for four, six or eight weeks, and the control mice, are euthanized, perfused, and selected organs analyzed for biomarkers of disease. Analyses of selected organs (e.g., brain, liver, spleen, lung, kidney, heart) include organ weight; IDUA specific enzyme activity, and GAG levels in tissue homogenates and histopathology of tissues stained for GAG and, in brain for GM3-gangliosides as done routinely by those skilled in the art (e.g., Ma et al. (2007); Hartung et al. (2004); Aronovich et al. (2009)). Using these techniques, the impact on brain of IDUA:RTB treatment is measured by quantitative morphometric analysis and behavioral testing comparing treated mice with untreated idua–/– mice. Additional analyses for assessing drug impacts on other specific organs and tissues such as the bone, eye, ear, and heart/aorta affected in idua$^{-/-}$ mice are also performed as described (e.g., Ma et al. (2007)). Experiments may also be expanded to included repeat IDUA:RTB administration (e.g., weekly or bi-weekly) of idua$^{-/-}$ mice started within 2 weeks of birth and analyzed at various periods to assess whether development of disease pathologies is avoided or significantly delayed compared to untreated idua$^{-/-}$ mice.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,938,949
U.S. Pat. No. 5,034,322
U.S. Pat. No. 5,106,739
U.S. Pat. No. 5,589,610
U.S. Pat. No. 5,625,136
U.S. Pat. No. 5,639,948
U.S. Pat. No. 5,661,017
U.S. Pat. No. 5,705,484
U.S. Pat. No. 6,455,760
U.S. Pat. No. 6,462,185
U.S. Pat. No. 6,696,623
U.S. Pat. No. 6,884,419
U.S. Pat. No. 7,011,972
U.S. Pat. No. 7,410,779
U.S. Pat. No. 7,867,972
U.S. Pat. No. 7,964,377
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
European Application No. EP1528104
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Aronovich et al. (2009) Mol Therapy 17(7): 1136-1144.
Bachmeier et al. (2006) Drug Metab. Dispos. Biolog. Fate Chem. 34(6):998-1003.
Becker D. (1990) Nucleic Acids Res. 18(1):203.
Cacchelli et al., (2007) Nature Rev. Drug Discovery 6:650-665.
Chen et al. (2010) BioTechniques 49:513-518.
Clancy, M. and Hannah, L. C. (2002) "Splicing of the maize Shl first intron is essential for enhancement of gene expression, and a T-rich motif increases expression without affecting splicing" *Plant Physiol.* 130(2):918-29.
Esposito et al., (2000). Biochim. Biophys. Acta 1501(1):1-11.
Förster, C. *Histochem Cell Biol* (2008) 130:55-70.
Furtado, A. et al. (2002) "Tools for Use in the Genetic Engineering of Barley" *Proceedings of the 10$^{th}$ Australian Barley Technical Symposium*, Canberra, ACT, Australia.
Gaddy-Kurten et al. (2002) Endrocrinology 143:74-84.
Good, X. et al. (1994) "Reduced ethylene synthesis by transgenic tomatoes expressing S-adenosylmethionine hydrolase" *Plant Molec. Biol.* 26:781-790.
Hartung et al. (2004) Mol Therapy 9(6):866-875.
Hwang, Y-S. et al. (2002) "Analysis of the Rice Endosperm-Specific Globulin Promoter in Transformed Rice Cells" *Plant Cell Rep.* 20:842-847.
Jørgensen et al., (2004) Steroid 69:219-226
Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecular Sequences" *Proc. Natl. Acad. Sci. USA* 90:5873-5877.
Lazarenko et al. (2006) Bone 38(1):74-84.
Lewin, B. (1985) *Genes II*, John Wiley & Sons, Inc., p. 96.
Liu J, Dolan M C, Cramer C L, unpublished data
Lovrinovic and Niemeyer (2005) BBRC 335:943-948.
Lungwitz et al. (2005) *Eur. J. Pharmacet. Bioparmacet.* 60:247-266.
Ma et al. (2007) Mol. Therapy 15(5): 889-902.
Malaval et al. (1994), J. Cellul. Physiol. 158:555-572.
Medrano et al. (2009) *In Methods in Biotechnology: Recombinant Proteins from Plants*, L. Faye, V. Gomond, eds., Humana Press, USA, pp. 51-68.
Montfort et al. (1987) J. Biol. Chem. 262(11):5398-5403.
Robinson and Sauer (1998) Proc. Natl. Acad. Sci. USA 95:5929-5934.
Ohmi et al. (2003) Proc. Natl. Acad. Sci USA 100:1902-1907.
Panchision et al. (2007) Stem Cells 25(6):1560-70.
Tessitore et al. (2004) Mol Cell 15(5):753-766.
Winchester B, Vellodi A, Young E (2000) *Biochem. Soc. Trans.* 28 (2):150-4.
Wu, C-L. et al. (1998) "Promoters of Rice Seed Storage Protein Genes Direct Endosperm-Specific Gene Expression in Transgenic Rice" *Plant and Cell Physiology*, 39(8):885-889.
Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.
Yuan et al. (2011) PLoS ONE 6(3): e17540.

Bie et al. "Crystal structure analysis of human alpha-L-iduroni two crystal forms" GenBank accession number pbd/4JXP_A version GI:480312357.

Scott et al. "Human alpha-L-iduronidase: cDNA isolation and expression" *Proc. Natl. Acad. Sci. U.S.A.* 88 (21), 9695-9699 (1991).

Matz et al. "Fluorescent proteins from nonbioluminescent Anthozoa species" Nat. Biotechnol. 17(10), 969-973 (1999).

Van Damme et al. "Characterization and molecular cloning of *Sambucus nigra* agglutinin V (nigrin b), a GalNAc-specific type-2 ribosome-inactivating protein from the bark of elderberry (*Sambucus nigra*)" *Eur. J. Biochem.* 237 (2), 505-513 (1996).

Maveyraud et al. "Structural basis for sugar recognition, including the to carcinoma antigen, by the lectin sna-ii from *sambucus nigra*" Proteins 75 p. 89 (2009).

Van de Kamp et al. "Genetic heterogeneity and clinical variability in the Sanfilippo syndrome (type A, B, and C)" *Clin. Genet.* 20 (2), 152-160 (1981).

Montfort et al. "The three-dimensional structure of ricin at 2.8A" *J. Biol Chem.* 262 (11), 5398-5403 (1987).

Audi J, Belson M, Patel M, Schier J, Osterloh J: (2005) JAMA 294(18):2342-2351.

Citores L, Munoz R, Rojo M A, Jimenez P, Ferreras J M, Girbes T (2003) Cell. Molec. Biol. 49:461-465.

Citores L, Munoz R, De Benito F M, Iglesias R, Ferreras J M, Girbes T (1996) Cell. Molec. Biol. 42(4):473-476.

Ferreras et al., (2011) *Toxins* 3: 420-441.

Hao et al. (2001) Plant Physiol. 125:866-876.

Sandvig K, van Deurs B (1999) FEBS Lett 452(1-2):67-70.

Simmons B M, Stahl P D, Russell J H (1986) J Biol Chem 261(17):7912-7920.

Van Damme et al., (1998) Crit. Rev. Plant Sci. 17: 575-692.

Bevan et al. "The structure and transcription start site of a major potato tuber protein gene" *Nucleic Acid Res.* 14 (11), 4625-4638 (1986).

---

I claim:

1. A compound comprising:
   a) a therapeutic agent or compound comprising a lysosomal enzyme; and
   b) a protein comprising a lectin from the B subunit of ricin or nigrin B that mediates delivery across the blood brain barrier;
   wherein said therapeutic agent or compound is physically linked or fused to said protein comprising said lectin; and wherein said compound comprises an amino acid sequence that is at least 90% identical to the amino acid sequences selected from the group consisting of SEQ ID NO: 1, SEQ ID NO: 2, SEQ ID NO: 4, SEQ ID NO: 5, SEQ ID NO: 6, SEQ ID NO: 7, SEQ ID NO: 9, and SEQ ID NO: 10.

2. A method for treating mucopolysaccharidosis type I in a person or animal comprising administering a therapeutically effective amount of the compound of claim 1 to said person or animal, thereby treating said mucopolysaccharidosis type I.

3. The compound of claim 1, wherein said compound comprises the amino acid sequence of SEQ ID NO: 6.

4. The compound of claim 1, wherein said compound comprises the amino acid sequence of SEQ ID NO: 7.

5. The compound of claim 1, wherein said compound comprises the amino acid sequence of SEQ ID NO: 9.

6. The compound of claim 1, wherein said compound comprises the amino acid sequence of SEQ ID NO: 10.

7. The compound of claim 1, wherein said compound comprises the amino acid sequence of SEQ ID NO: 1.

8. The compound of claim 1, wherein said compound comprises the amino acid sequence of SEQ ID NO: 2.

9. The compound of claim 1, wherein said compound comprises the amino acid sequence of SEQ ID NO: 4.

10. The compound of claim 1, wherein said compound comprises the amino acid sequence of SEQ ID NO: 5.

11. A method for treating mucopolysaccharidosis type IIIA in a person or animal comprising administering a therapeutically effective amount of the compound of claim 1 to said person or animal, thereby treating said mucopolysaccharidosis type IIIA.

12. The method of claim 2, wherein said compound comprises the amino acid sequence of SEQ ID NO:6.

13. The method of claim 2, wherein said compound comprises the amino acid sequence of SEQ ID NO:7.

14. The method of claim 2, wherein said compound comprises the amino acid sequence of SEQ ID NO:9.

15. The method of claim 2, wherein said compound comprises the amino acid sequence of SEQ ID NO:10.

16. The method of claim 11, wherein said compound comprises the amino acid sequence of SEQ ID NO:6.

17. The method of claim 11, wherein said compound comprises the amino acid sequence of SEQ ID NO:7.

18. The method of claim 11, wherein said compound comprises the amino acid sequence of SEQ ID NO:9.

19. The method of claim 11, wherein said compound comprises the amino acid sequence of SEQ ID NO:10.

* * * * *

UNITED STATES PATENT AND TRADEMARK OFFICE
CERTIFICATE OF CORRECTION

PATENT NO. : 9,862,939 B2
APPLICATION NO. : 14/956001
DATED : January 9, 2018
INVENTOR(S) : David N. Radin and Carole L. Cramer Page 1 of 1

It is certified that error appears in the above-identified patent and that said Letters Patent is hereby corrected as shown below:

In the Specification

Column 9,
Line 10, "$[P(33 + 29)]_3$" should read --$[P(33 + 29)]_2$--.
Line 13, "$[P(30 + 33)]_1$" should read --$[P(30 + 33)]_2$--.
Line 16, "$[P(28 + 30)]_1$" should read --$[P(28 + 30)]_2$--.
Line 24, "$I[P(32 + 36)]_4$" should read --$I[P(32 + 35)]_4$--.
Line 25, "$I'[P(32 + 36)]_2$" should read --$I'[P(32 + 35)]_2$--.

Column 11,
Line 28, "AMPS III" should read --A/MPS III--.

Column 12,
Lines 29-30, "a-galactosidase" should read --α-galactosidase--.

Column 13,
Line 41, "a-L-iduronidase" should read --α-L-iduronidase--.

Column 14,
Line 17, "the to carcinoma" should read --the tn carcinoma--.
Line 19, "NP 000190.1" should read --NP_000190.1--.

Column 21,
Line 34, "and)(BLAST" should read --and XBLAST--.
Line 41, "and)(BLAST)" should read --and XBLAST)--.

Signed and Sealed this
Sixteenth Day of October, 2018

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 919
<212> TYPE: PRT
<213> ORGANISM: Artificial sequence
<220> FEATURE:
<223> OTHER INFORMATION: Fusion protein

<400> SEQUENCE: 1

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Glu Ala Pro His
                20                  25                  30

Leu Val Gln Val Asp Ala Ala Arg Ala Leu Trp Pro Leu Arg Arg Phe
            35                  40                  45

Trp Arg Ser Thr Gly Phe Cys Pro Pro Leu Pro His Ser Gln Ala Asp
        50                  55                  60

Gln Tyr Val Leu Ser Trp Asp Gln Gln Leu Asn Leu Ala Tyr Val Gly
65                  70                  75                  80

Ala Val Pro His Arg Gly Ile Lys Gln Val Arg Thr His Trp Leu Leu
                85                  90                  95

Glu Leu Val Thr Thr Arg Gly Ser Thr Gly Arg Gly Leu Ser Tyr Asn
                100                 105                 110

Phe Thr His Leu Asp Gly Tyr Leu Asp Leu Leu Arg Glu Asn Gln Leu
            115                 120                 125

Leu Pro Gly Phe Glu Leu Met Gly Ser Ala Ser Gly His Phe Thr Asp
        130                 135                 140

Phe Glu Asp Lys Gln Gln Val Phe Glu Trp Lys Asp Leu Val Ser Ser
145                 150                 155                 160

Leu Ala Arg Arg Tyr Ile Gly Arg Tyr Gly Leu Ala His Val Ser Lys
                165                 170                 175

Trp Asn Phe Glu Thr Trp Asn Glu Pro Asp His His Asp Phe Asp Asn
                180                 185                 190

Val Ser Met Thr Met Gln Gly Phe Leu Asn Tyr Tyr Asp Ala Cys Ser
            195                 200                 205

Glu Gly Leu Arg Ala Ala Ser Pro Ala Leu Arg Leu Gly Gly Pro Gly
        210                 215                 220
```

-continued

```
Asp Ser Phe His Thr Pro Pro Arg Ser Pro Leu Ser Trp Gly Leu Leu
225                 230                 235                 240

Arg His Cys His Asp Gly Thr Asn Phe Phe Thr Gly Glu Ala Gly Val
            245                 250                 255

Arg Leu Asp Tyr Ile Ser Leu His Arg Lys Gly Ala Arg Ser Ser Ile
        260                 265                 270

Ser Ile Leu Glu Gln Glu Lys Val Val Ala Gln Gln Ile Arg Gln Leu
    275                 280                 285

Phe Pro Lys Phe Ala Asp Thr Pro Ile Tyr Asn Asp Glu Ala Asp Pro
290                 295                 300

Leu Val Gly Trp Ser Leu Pro Gln Pro Trp Arg Ala Asp Val Thr Tyr
305                 310                 315                 320

Ala Ala Met Val Val Lys Val Ile Ala Gln His Gln Asn Leu Leu Leu
                325                 330                 335

Ala Asn Thr Thr Ser Ala Phe Pro Tyr Ala Leu Leu Ser Asn Asp Asn
            340                 345                 350

Ala Phe Leu Ser Tyr His Pro His Pro Phe Ala Gln Arg Thr Leu Thr
        355                 360                 365

Ala Arg Phe Gln Val Asn Asn Thr Arg Pro Pro His Val Gln Leu Leu
370                 375                 380

Arg Lys Pro Val Leu Thr Ala Met Gly Leu Leu Ala Leu Leu Asp Glu
385                 390                 395                 400

Glu Gln Leu Trp Ala Glu Val Ser Gln Ala Gly Thr Val Leu Asp Ser
                405                 410                 415

Asn His Thr Val Gly Val Leu Ala Ser Ala His Arg Pro Gln Gly Pro
            420                 425                 430

Ala Asp Ala Trp Arg Ala Ala Val Leu Ile Tyr Ala Ser Asp Asp Thr
        435                 440                 445

Arg Ala His Pro Asn Arg Ser Val Ala Val Thr Leu Arg Leu Arg Gly
    450                 455                 460

Val Pro Pro Gly Pro Gly Leu Val Tyr Val Thr Arg Tyr Leu Asp Asn
465                 470                 475                 480

Gly Leu Cys Ser Pro Asp Gly Glu Trp Arg Arg Leu Gly Arg Pro Val
                485                 490                 495

Phe Pro Thr Ala Glu Gln Phe Arg Arg Met Arg Ala Ala Glu Asp Pro
            500                 505                 510

Val Ala Ala Pro Arg Pro Leu Pro Ala Gly Gly Arg Leu Thr Leu
        515                 520                 525

Arg Pro Ala Leu Arg Leu Pro Ser Leu Leu Val His Val Cys Ala
530                 535                 540

Arg Pro Glu Lys Pro Pro Gly Gln Val Thr Arg Leu Arg Ala Leu Pro
545                 550                 555                 560

Leu Thr Gln Gly Gln Leu Val Leu Val Trp Ser Asp Glu His Val Gly
                565                 570                 575

Ser Lys Cys Leu Trp Thr Tyr Glu Ile Gln Phe Ser Gln Asp Gly Lys
            580                 585                 590

Ala Tyr Thr Pro Val Ser Arg Lys Pro Ser Thr Phe Asn Leu Phe Val
        595                 600                 605

Phe Ser Pro Asp Thr Gly Ala Val Ser Gly Ser Tyr Arg Val Arg Ala
    610                 615                 620

Leu Asp Tyr Trp Ala Arg Pro Gly Pro Phe Ser Asp Pro Val Pro Tyr
625                 630                 635                 640

Leu Glu Val Pro Val Pro Arg Gly Pro Pro Ser Pro Gly Asn Pro Leu
```

-continued

```
                645                 650                 655
Glu Pro Glu Pro Ile Val Arg Ile Val Gly Arg Asn Gly Leu Cys Val
            660                 665                 670
Asp Val Arg Asp Gly Arg Phe His Asn Gly Asn Ala Ile Gln Leu Trp
        675                 680                 685
Pro Cys Lys Ser Asn Thr Asp Ala Asn Gln Leu Trp Thr Leu Lys Arg
    690                 695                 700
Asp Asn Thr Ile Arg Ser Asn Gly Lys Cys Leu Thr Thr Tyr Gly Tyr
705                 710                 715                 720
Ser Pro Gly Val Tyr Val Met Ile Tyr Asp Cys Asn Thr Ala Ala Thr
                725                 730                 735
Asp Ala Thr Arg Trp Gln Ile Trp Asp Asn Gly Thr Ile Ile Asn Pro
            740                 745                 750
Arg Ser Ser Leu Val Leu Ala Ala Thr Ser Gly Asn Ser Gly Thr Thr
        755                 760                 765
Leu Thr Val Gln Thr Asn Ile Tyr Ala Val Ser Gln Gly Trp Leu Pro
    770                 775                 780
Thr Asn Asn Thr Gln Pro Phe Val Thr Thr Ile Val Gly Leu Tyr Gly
785                 790                 795                 800
Leu Cys Leu Gln Ala Asn Ser Gly Gln Val Trp Ile Glu Asp Cys Ser
                805                 810                 815
Ser Glu Lys Ala Glu Gln Gln Trp Ala Leu Tyr Ala Asp Gly Ser Ile
            820                 825                 830
Arg Pro Gln Gln Asn Arg Asp Asn Cys Leu Thr Ser Asp Ser Asn Ile
        835                 840                 845
Arg Glu Thr Val Val Lys Ile Leu Ser Cys Gly Pro Ala Ser Ser Gly
    850                 855                 860
Gln Arg Trp Met Phe Lys Asn Asp Gly Thr Ile Leu Asn Leu Tyr Ser
865                 870                 875                 880
Gly Leu Val Leu Asp Val Arg Ala Ser Asp Pro Ser Leu Lys Gln Ile
                885                 890                 895
Ile Leu Tyr Pro Leu His Gly Asp Pro Asn Gln Ile Trp Leu Pro Leu
            900                 905                 910
Phe His His His His His
        915
```

<210> SEQ ID NO 2
<211> LENGTH: 930
<212> TYPE: PRT
<213> ORGANISM: Artificial sequence
<220> FEATURE:
<223> OTHER INFORMATION: Fusion protein

<400> SEQUENCE: 2

```
Met Ala Ser Ser Ala Thr Thr Lys Ser Phe Leu Ile Leu Phe Phe Met
1               5                   10                  15
Ile Leu Ala Thr Thr Ser Ser Thr Cys Ala Val Asp Glu Ala Pro His
                20                  25                  30
Leu Val Gln Val Asp Ala Ala Arg Ala Leu Trp Pro Leu Arg Arg Phe
        35                  40                  45
Trp Arg Ser Thr Gly Phe Cys Pro Pro Leu Pro His Ser Gln Ala Asp
    50                  55                  60
Gln Tyr Val Leu Ser Trp Asp Gln Gln Leu Asn Leu Ala Tyr Val Gly
65                  70                  75                  80
Ala Val Pro His Arg Gly Ile Lys Gln Val Arg Thr His Trp Leu Leu
```

```
                      85                  90                  95
        Glu Leu Val Thr Thr Arg Gly Ser Thr Gly Arg Gly Leu Ser Tyr Asn
                        100                 105                 110

Phe Thr His Leu Asp Gly Tyr Leu Asp Leu Leu Arg Glu Asn Gln Leu
                115                 120                 125

Leu Pro Gly Phe Glu Leu Met Gly Ser Ala Ser Gly His Phe Thr Asp
                130                 135                 140

Phe Glu Asp Lys Gln Gln Val Phe Glu Trp Lys Asp Leu Val Ser Ser
        145                 150                 155                 160

Leu Ala Arg Arg Tyr Ile Gly Arg Tyr Gly Leu Ala His Val Ser Lys
                        165                 170                 175

Trp Asn Phe Glu Thr Trp Asn Glu Pro Asp His His Asp Phe Asp Asn
                        180                 185                 190

Val Ser Met Thr Met Gln Gly Phe Leu Asn Tyr Tyr Asp Ala Cys Ser
                        195                 200                 205

Glu Gly Leu Arg Ala Ala Ser Pro Ala Leu Arg Leu Gly Gly Pro Gly
                        210                 215                 220

Asp Ser Phe His Thr Pro Pro Arg Ser Pro Leu Ser Trp Gly Leu Leu
        225                 230                 235                 240

Arg His Cys His Asp Gly Thr Asn Phe Phe Thr Gly Glu Ala Gly Val
                            245                 250                 255

Arg Leu Asp Tyr Ile Ser Leu His Arg Lys Gly Ala Arg Ser Ser Ile
                        260                 265                 270

Ser Ile Leu Glu Gln Glu Lys Val Val Ala Gln Gln Ile Arg Gln Leu
                        275                 280                 285

Phe Pro Lys Phe Ala Asp Thr Pro Ile Tyr Asn Asp Glu Ala Asp Pro
                        290                 295                 300

Leu Val Gly Trp Ser Leu Pro Gln Pro Trp Arg Ala Asp Val Thr Tyr
        305                 310                 315                 320

Ala Ala Met Val Val Lys Val Ile Ala Gln His Gln Asn Leu Leu Leu
                        325                 330                 335

Ala Asn Thr Thr Ser Ala Phe Pro Tyr Ala Leu Leu Ser Asn Asp Asn
                        340                 345                 350

Ala Phe Leu Ser Tyr His Pro His Pro Phe Ala Gln Arg Thr Leu Thr
                        355                 360                 365

Ala Arg Phe Gln Val Asn Asn Thr Arg Pro Pro His Val Gln Leu Leu
                        370                 375                 380

Arg Lys Pro Val Leu Thr Ala Met Gly Leu Leu Ala Leu Leu Asp Glu
        385                 390                 395                 400

Glu Gln Leu Trp Ala Glu Val Ser Gln Ala Gly Thr Val Leu Asp Ser
                        405                 410                 415

Asn His Thr Val Gly Val Leu Ala Ser Ala His Arg Pro Gln Gly Pro
                        420                 425                 430

Ala Asp Ala Trp Arg Ala Ala Val Leu Ile Tyr Ala Ser Asp Asp Thr
                        435                 440                 445

Arg Ala His Pro Asn Arg Ser Val Ala Val Thr Leu Arg Leu Arg Gly
                        450                 455                 460

Val Pro Pro Gly Pro Gly Leu Val Tyr Val Thr Arg Tyr Leu Asp Asn
        465                 470                 475                 480

Gly Leu Cys Ser Pro Asp Gly Glu Trp Arg Arg Leu Gly Arg Pro Val
                        485                 490                 495

Phe Pro Thr Ala Glu Gln Phe Arg Arg Met Arg Ala Ala Glu Asp Pro
                        500                 505                 510
```

```
Val Ala Ala Pro Arg Pro Leu Pro Ala Gly Gly Arg Leu Thr Leu
            515                 520                 525

Arg Pro Ala Leu Arg Leu Pro Ser Leu Leu Leu Val His Val Cys Ala
530                 535                 540

Arg Pro Glu Lys Pro Pro Gly Gln Val Thr Arg Leu Arg Ala Leu Pro
545                 550                 555                 560

Leu Thr Gln Gly Gln Leu Val Leu Val Trp Ser Asp Glu His Val Gly
                565                 570                 575

Ser Lys Cys Leu Trp Thr Tyr Glu Ile Gln Phe Ser Gln Asp Gly Lys
                580                 585                 590

Ala Tyr Thr Pro Val Ser Arg Lys Pro Ser Thr Phe Asn Leu Phe Val
        595                 600                 605

Phe Ser Pro Asp Thr Gly Ala Val Ser Gly Ser Tyr Arg Val Arg Ala
        610                 615                 620

Leu Asp Tyr Trp Ala Arg Pro Gly Pro Phe Ser Asp Pro Val Pro Tyr
625                 630                 635                 640

Leu Glu Val Pro Val Pro Arg Gly Pro Pro Ser Pro Gly Asn Pro Leu
                645                 650                 655

Glu Gly Glu Thr Ser Thr Leu Arg Thr Ser Phe Thr Arg Asn Ile Val
            660                 665                 670

Gly Arg Asp Gly Leu Cys Val Asp Val Arg Asn Gly Tyr Asp Thr Asp
        675                 680                 685

Gly Thr Pro Leu Gln Leu Trp Pro Cys Gly Thr Gln Arg Asn Gln Arg
    690                 695                 700

Trp Thr Phe Asp Ser Asp Thr Ile Arg Ser Met Gly Lys Cys Met
705                 710                 715                 720

Thr Ala Asn Gly Leu Asn Asn Gly Ser Asn Ile Val Ile Phe Asn Cys
                725                 730                 735

Ser Thr Ala Ala Glu Asn Ala Ile Lys Trp Glu Val Pro Ile Asp Gly
            740                 745                 750

Ser Ile Ile Asn Pro Ser Ser Gly Leu Val Met Thr Ala Pro Arg Ala
        755                 760                 765

Ala Ser Arg Thr Ile Leu Leu Leu Glu Asp Asn Ile Tyr Ala Ala Ser
770                 775                 780

Gln Gly Trp Thr Val Thr Asn Asn Val Lys Pro Ile Val Ala Ser Ile
785                 790                 795                 800

Val Gly Tyr Lys Glu Met Cys Leu Gln Ser Asn Gly Glu Asn Asn Gly
                805                 810                 815

Val Trp Met Glu Asp Cys Glu Ala Thr Ser Leu Gln Gln Trp Ala
                820                 825                 830

Leu Tyr Gly Asp Arg Thr Ile Arg Val Asn Ser Thr Arg Gly Leu Cys
        835                 840                 845

Val Thr Thr Asn Gly Tyr Asn Ser Lys Asp Leu Ile Ile Ile Leu Lys
850                 855                 860

Cys Gln Gly Leu Pro Ser Gln Arg Trp Phe Phe Asn Ser Asp Gly Ala
865                 870                 875                 880

Ile Val Asn Pro Lys Ser Arg His Val Met Asp Val Arg Ala Ser Asn
                885                 890                 895

Val Ser Leu Arg Glu Ile Ile Ile Phe Pro Ala Thr Gly Asn Pro Asn
            900                 905                 910

Gln Gln Trp Val Thr Gln Val Leu Pro Ser Pro Gly His His His
        915                 920                 925
```

His His
    930

<210> SEQ ID NO 3
<211> LENGTH: 527
<212> TYPE: PRT
<213> ORGANISM: Artificial sequence
<220> FEATURE:
<223> OTHER INFORMATION: Fusion protein

<400> SEQUENCE: 3

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Val Arg Ser Ser Lys
            20                  25                  30

Asn Val Ile Lys Glu Phe Met Arg Phe Lys Val Arg Met Glu Gly Thr
        35                  40                  45

Val Asn Gly His Glu Phe Glu Ile Glu Gly Glu Gly Glu Gly Arg Pro
    50                  55                  60

Tyr Glu Gly His Asn Thr Val Lys Leu Lys Val Thr Lys Gly Gly Pro
65                  70                  75                  80

Leu Pro Phe Ala Trp Asp Ile Leu Ser Pro Gln Phe Gln Tyr Gly Ser
                85                  90                  95

Lys Val Tyr Val Lys His Pro Ala Asp Ile Pro Asp Tyr Lys Lys Leu
            100                 105                 110

Ser Phe Pro Glu Gly Phe Lys Trp Glu Arg Val Met Asn Phe Glu Asp
        115                 120                 125

Gly Gly Val Val Thr Val Thr Gln Asp Ser Ser Leu Gln Asp Gly Cys
    130                 135                 140

Phe Ile Tyr Lys Val Lys Phe Ile Gly Val Asn Phe Pro Ser Asp Gly
145                 150                 155                 160

Pro Val Met Gln Lys Lys Thr Met Gly Trp Glu Ala Ser Thr Glu Arg
                165                 170                 175

Leu Tyr Pro Arg Asp Gly Val Leu Lys Gly Glu Ile His Lys Ala Leu
            180                 185                 190

Lys Leu Lys Asp Gly Gly His Tyr Leu Val Glu Phe Lys Ser Ile Tyr
        195                 200                 205

Met Ala Lys Lys Pro Val Gln Leu Pro Gly Tyr Tyr Tyr Val Asp Ser
    210                 215                 220

Lys Leu Asp Ile Thr Ser His Asn Glu Asp Tyr Thr Ile Val Glu Gln
225                 230                 235                 240

Tyr Glu Arg Thr Glu Gly Arg His His Leu Phe Leu Glu Gly Glu
                245                 250                 255

Thr Ser Thr Leu Arg Thr Ser Phe Thr Arg Asn Ile Val Gly Arg Asp
            260                 265                 270

Gly Leu Cys Val Asp Val Arg Asn Gly Tyr Asp Thr Asp Gly Thr Pro
        275                 280                 285

Leu Gln Leu Trp Pro Cys Gly Thr Gln Arg Asn Gln Arg Trp Thr Phe
    290                 295                 300

Asp Ser Asp Asp Thr Ile Arg Ser Met Gly Lys Cys Met Thr Ala Asn
305                 310                 315                 320

Gly Leu Asn Asn Gly Ser Asn Ile Val Ile Phe Asn Cys Ser Thr Ala
                325                 330                 335

Ala Glu Asn Ala Ile Lys Trp Glu Val Pro Ile Asp Gly Ser Ile Ile
            340                 345                 350

```
Asn Pro Ser Ser Gly Leu Val Met Thr Ala Pro Arg Ala Ala Ser Arg
            355                 360                 365

Thr Ile Leu Leu Leu Glu Asp Asn Ile Tyr Ala Ala Ser Gln Gly Trp
    370                 375                 380

Thr Val Thr Asn Asn Val Lys Pro Ile Val Ala Ser Ile Val Gly Tyr
385                 390                 395                 400

Lys Glu Met Cys Leu Gln Ser Asn Gly Glu Asn Asn Gly Val Trp Met
                405                 410                 415

Glu Asp Cys Glu Ala Thr Ser Leu Gln Gln Trp Ala Leu Tyr Gly
            420                 425                 430

Asp Arg Thr Ile Arg Val Asn Ser Thr Arg Gly Leu Cys Val Thr Thr
            435                 440                 445

Asn Gly Tyr Asn Ser Lys Asp Leu Ile Ile Ile Leu Lys Cys Gln Gly
    450                 455                 460

Leu Pro Ser Gln Arg Trp Phe Phe Asn Ser Asp Gly Ala Ile Val Asn
465                 470                 475                 480

Pro Lys Ser Arg His Val Met Asp Val Arg Ala Ser Asn Val Ser Leu
                485                 490                 495

Arg Glu Ile Ile Ile Phe Pro Ala Thr Gly Asn Pro Asn Gln Gln Trp
            500                 505                 510

Val Thr Gln Val Leu Pro Ser Pro Gly His His His His His His
            515                 520                 525

<210> SEQ ID NO 4
<211> LENGTH: 783
<212> TYPE: PRT
<213> ORGANISM: Artificial sequence
<220> FEATURE:
<223> OTHER INFORMATION: Fusion protein

<400> SEQUENCE: 4

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Gly Glu Thr Ser
            20                  25                  30

Thr Leu Arg Thr Ser Phe Thr Arg Asn Ile Val Gly Arg Asp Gly Leu
        35                  40                  45

Cys Val Asp Val Arg Asn Gly Tyr Asp Thr Asp Gly Thr Pro Leu Gln
    50                  55                  60

Leu Trp Pro Cys Gly Thr Gln Arg Asn Gln Arg Trp Thr Phe Asp Ser
65                  70                  75                  80

Asp Asp Thr Ile Arg Ser Met Gly Lys Cys Met Thr Ala Asn Gly Leu
                85                  90                  95

Asn Asn Gly Ser Asn Ile Val Ile Phe Asn Cys Ser Thr Ala Ala Glu
            100                 105                 110

Asn Ala Ile Lys Trp Glu Val Pro Ile Asp Gly Ser Ile Ile Asn Pro
        115                 120                 125

Ser Ser Gly Leu Val Met Thr Ala Pro Arg Ala Ala Ser Arg Thr Ile
    130                 135                 140

Leu Leu Leu Glu Asp Asn Ile Tyr Ala Ala Ser Gln Gly Trp Thr Val
145                 150                 155                 160

Thr Asn Asn Val Lys Pro Ile Val Ala Ser Ile Val Gly Tyr Lys Glu
                165                 170                 175

Met Cys Leu Gln Ser Asn Gly Glu Asn Asn Gly Val Trp Met Glu Asp
            180                 185                 190
```

```
Cys Glu Ala Thr Ser Leu Gln Gln Gln Trp Ala Leu Tyr Gly Asp Arg
        195                 200                 205

Thr Ile Arg Val Asn Ser Thr Arg Gly Leu Cys Val Thr Thr Asn Gly
    210                 215                 220

Tyr Asn Ser Lys Asp Leu Ile Ile Ile Leu Lys Cys Gln Gly Leu Pro
225                 230                 235                 240

Ser Gln Arg Trp Phe Phe Asn Ser Asp Gly Ala Ile Val Asn Pro Lys
                245                 250                 255

Ser Arg His Val Met Asp Val Arg Ala Ser Asn Val Ser Leu Arg Glu
            260                 265                 270

Ile Ile Ile Phe Pro Ala Thr Gly Asn Pro Asn Gln Gln Trp Val Thr
        275                 280                 285

Gln Val Leu Pro Ser Leu Glu Arg Pro Arg Asn Ala Leu Leu Leu Leu
    290                 295                 300

Ala Asp Asp Gly Gly Phe Glu Ser Gly Ala Tyr Asn Asn Ser Ala Ile
305                 310                 315                 320

Ala Thr Pro His Leu Asp Ala Leu Ala Arg Arg Ser Leu Leu Phe Arg
                325                 330                 335

Asn Ala Phe Thr Ser Val Ser Ser Cys Ser Pro Ser Arg Ala Ser Leu
            340                 345                 350

Leu Thr Gly Leu Pro Gln His Gln Asn Gly Met Tyr Gly Leu His Gln
        355                 360                 365

Asp Val His His Phe Asn Ser Phe Asp Lys Val Arg Ser Leu Pro Leu
    370                 375                 380

Leu Leu Ser Gln Ala Gly Val Arg Thr Gly Ile Ile Gly Lys Lys His
385                 390                 395                 400

Val Gly Pro Glu Thr Val Tyr Pro Phe Asp Phe Ala Tyr Thr Glu Glu
                405                 410                 415

Asn Gly Ser Val Leu Gln Val Gly Arg Asn Ile Thr Arg Ile Lys Leu
            420                 425                 430

Leu Val Arg Lys Phe Leu Gln Thr Gln Asp Asp Arg Pro Phe Phe Leu
        435                 440                 445

Tyr Val Ala Phe His Asp Pro His Arg Cys Gly His Ser Gln Pro Gln
450                 455                 460

Tyr Gly Thr Phe Cys Glu Lys Phe Gly Asn Gly Glu Ser Gly Met Gly
465                 470                 475                 480

Arg Ile Pro Asp Trp Thr Pro Gln Ala Tyr Asp Pro Leu Asp Val Leu
                485                 490                 495

Val Pro Tyr Phe Val Pro Asn Thr Pro Ala Ala Arg Ala Asp Leu Ala
            500                 505                 510

Ala Gln Tyr Thr Thr Val Gly Arg Met Asp Gln Gly Val Gly Leu Val
        515                 520                 525

Leu Gln Glu Leu Arg Asp Ala Gly Val Leu Asn Asp Thr Leu Val Ile
    530                 535                 540

Phe Thr Ser Asp Asn Gly Ile Pro Phe Pro Ser Gly Arg Thr Asn Leu
545                 550                 555                 560

Tyr Trp Pro Gly Thr Ala Glu Pro Leu Leu Val Ser Ser Pro Glu His
                565                 570                 575

Pro Lys Arg Trp Gly Gln Val Ser Glu Ala Tyr Val Ser Leu Leu Asp
            580                 585                 590

Leu Thr Pro Thr Ile Leu Asp Trp Phe Ser Ile Pro Tyr Pro Ser Tyr
        595                 600                 605

Ala Ile Phe Gly Ser Lys Thr Ile His Leu Thr Gly Arg Ser Leu Leu
```

```
            610             615             620
Pro Ala Leu Glu Ala Glu Pro Leu Trp Ala Thr Val Phe Gly Ser Gln
625             630             635             640

Ser His His Glu Val Thr Met Ser Tyr Pro Met Arg Ser Val Gln His
            645             650             655

Arg His Phe Arg Leu Val His Asn Leu Asn Phe Lys Met Pro Phe Pro
                660             665             670

Ile Asp Gln Asp Phe Tyr Val Ser Pro Thr Phe Gln Asp Leu Leu Asn
            675             680             685

Arg Thr Thr Ala Gly Gln Pro Thr Gly Trp Tyr Lys Asp Leu Arg His
        690             695             700

Tyr Tyr Tyr Arg Ala Arg Trp Glu Leu Tyr Asp Arg Ser Arg Asp Pro
705             710             715             720

His Glu Thr Gln Asn Leu Ala Thr Asp Pro Arg Phe Ala Gln Leu Leu
                725             730             735

Glu Met Leu Arg Asp Gln Leu Ala Lys Trp Gln Trp Glu Thr His Asp
            740             745             750

Pro Trp Val Cys Ala Pro Asp Gly Val Leu Glu Glu Lys Leu Ser Pro
        755             760             765

Gln Cys Gln Pro Leu His Asn Glu Leu His His His His His His
770             775             780
```

<210> SEQ ID NO 5
<211> LENGTH: 766
<212> TYPE: PRT
<213> ORGANISM: Artificial sequence
<220> FEATURE:
<223> OTHER INFORMATION: Fusion protein

<400> SEQUENCE: 5

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
```

-continued

```
            195                 200                 205
Asp Trp Thr Pro Gln Ala Tyr Asp Pro Leu Asp Val Leu Val Pro Tyr
210                 215                 220
Phe Val Pro Asn Thr Pro Ala Ala Arg Ala Asp Leu Ala Ala Gln Tyr
225                 230                 235                 240
Thr Thr Val Gly Arg Met Asp Gln Gly Val Gly Leu Val Leu Gln Glu
                245                 250                 255
Leu Arg Asp Ala Gly Val Leu Asn Asp Thr Leu Val Ile Phe Thr Ser
                260                 265                 270
Asp Asn Gly Ile Pro Phe Pro Ser Gly Arg Thr Asn Leu Tyr Trp Pro
            275                 280                 285
Gly Thr Ala Glu Pro Leu Leu Val Ser Ser Pro Glu His Pro Lys Arg
290                 295                 300
Trp Gly Gln Val Ser Glu Ala Tyr Val Ser Leu Leu Asp Leu Thr Pro
305                 310                 315                 320
Thr Ile Leu Asp Trp Phe Ser Ile Pro Tyr Pro Ser Tyr Ala Ile Phe
                325                 330                 335
Gly Ser Lys Thr Ile His Leu Thr Gly Arg Ser Leu Leu Pro Ala Leu
                340                 345                 350
Glu Ala Glu Pro Leu Trp Ala Thr Val Phe Gly Ser Gln Ser His His
            355                 360                 365
Glu Val Thr Met Ser Tyr Pro Met Arg Ser Val Gln His Arg His Phe
370                 375                 380
Arg Leu Val His Asn Leu Asn Phe Lys Met Pro Phe Pro Ile Asp Gln
385                 390                 395                 400
Asp Phe Tyr Val Ser Pro Thr Phe Gln Asp Leu Leu Asn Arg Thr Thr
                405                 410                 415
Ala Gly Gln Pro Thr Gly Trp Tyr Lys Asp Leu Arg His Tyr Tyr Tyr
                420                 425                 430
Arg Ala Arg Trp Glu Leu Tyr Asp Arg Ser Arg Asp Pro His Glu Thr
            435                 440                 445
Gln Asn Leu Ala Thr Asp Pro Arg Phe Ala Gln Leu Leu Glu Met Leu
450                 455                 460
Arg Asp Gln Leu Ala Lys Trp Gln Trp Glu Thr His Asp Pro Trp Val
465                 470                 475                 480
Cys Ala Pro Asp Gly Val Leu Glu Glu Lys Leu Ser Pro Gln Cys Gln
                485                 490                 495
Pro Leu His Asn Glu Leu Leu Glu Pro Glu Pro Ile Val Arg Ile Val
                500                 505                 510
Gly Arg Asn Gly Leu Cys Val Asp Val Arg Asp Gly Arg Phe His Asn
            515                 520                 525
Gly Asn Ala Ile Gln Leu Trp Pro Cys Lys Ser Asn Thr Asp Ala Asn
530                 535                 540
Gln Leu Trp Thr Leu Lys Arg Asp Asn Thr Ile Arg Ser Asn Gly Lys
545                 550                 555                 560
Cys Leu Thr Thr Tyr Gly Tyr Ser Pro Gly Val Tyr Val Met Ile Tyr
                565                 570                 575
Asp Cys Asn Thr Ala Ala Thr Asp Ala Thr Arg Trp Gln Ile Trp Asp
                580                 585                 590
Asn Gly Thr Ile Ile Asn Pro Arg Ser Ser Leu Val Leu Ala Ala Thr
            595                 600                 605
Ser Gly Asn Ser Gly Thr Thr Leu Thr Val Gln Thr Asn Ile Tyr Ala
610                 615                 620
```

```
Val Ser Gln Gly Trp Leu Pro Thr Asn Asn Thr Gln Pro Phe Val Thr
625                 630                 635                 640

Thr Ile Val Gly Leu Tyr Gly Leu Cys Leu Gln Ala Asn Ser Gly Gln
                645                 650                 655

Val Trp Ile Glu Asp Cys Ser Ser Glu Lys Ala Glu Gln Gln Trp Ala
            660                 665                 670

Leu Tyr Ala Asp Gly Ser Ile Arg Pro Gln Gln Asn Arg Asp Asn Cys
        675                 680                 685

Leu Thr Ser Asp Ser Asn Ile Arg Glu Thr Val Val Lys Ile Leu Ser
    690                 695                 700

Cys Gly Pro Ala Ser Ser Gly Gln Arg Trp Met Phe Lys Asn Asp Gly
705                 710                 715                 720

Thr Ile Leu Asn Leu Tyr Ser Gly Leu Val Leu Asp Val Arg Ala Ser
                725                 730                 735

Asp Pro Ser Leu Lys Gln Ile Ile Leu Tyr Pro Leu His Gly Asp Pro
            740                 745                 750

Asn Gln Ile Trp Leu Pro Leu Phe His His His His His
        755                 760                 765

<210> SEQ ID NO 6
<211> LENGTH: 883
<212> TYPE: PRT
<213> ORGANISM: Artificial sequence
<220> FEATURE:
<223> OTHER INFORMATION: Fusion protein

<400> SEQUENCE: 6

Glu Ala Pro His Leu Val Gln Val Asp Ala Ala Arg Ala Leu Trp Pro
1               5                   10                  15

Leu Arg Arg Phe Trp Arg Ser Thr Gly Phe Cys Pro Pro Leu Pro His
            20                  25                  30

Ser Gln Ala Asp Gln Tyr Val Leu Ser Trp Asp Gln Gln Leu Asn Leu
        35                  40                  45

Ala Tyr Val Gly Ala Val Pro His Arg Gly Ile Lys Gln Val Arg Thr
    50                  55                  60

His Trp Leu Leu Glu Leu Val Thr Thr Arg Gly Ser Thr Gly Arg Gly
65                  70                  75                  80

Leu Ser Tyr Asn Phe Thr His Leu Asp Gly Tyr Leu Asp Leu Leu Arg
                85                  90                  95

Glu Asn Gln Leu Leu Pro Gly Phe Glu Leu Met Gly Ser Ala Ser Gly
            100                 105                 110

His Phe Thr Asp Phe Glu Asp Lys Gln Gln Val Phe Glu Trp Lys Asp
        115                 120                 125

Leu Val Ser Ser Leu Ala Arg Arg Tyr Ile Gly Arg Tyr Gly Leu Ala
    130                 135                 140

His Val Ser Lys Trp Asn Phe Glu Thr Trp Asn Glu Pro Asp His His
145                 150                 155                 160

Asp Phe Asp Asn Val Ser Met Thr Met Gln Gly Phe Leu Asn Tyr Tyr
                165                 170                 175

Asp Ala Cys Ser Glu Gly Leu Arg Ala Ala Ser Pro Ala Leu Arg Leu
            180                 185                 190

Gly Gly Pro Gly Asp Ser Phe His Thr Pro Pro Arg Ser Pro Leu Ser
        195                 200                 205

Trp Gly Leu Leu Arg His Cys His Asp Gly Thr Asn Phe Phe Thr Gly
    210                 215                 220
```

```
Glu Ala Gly Val Arg Leu Asp Tyr Ile Ser Leu His Arg Lys Gly Ala
225                 230                 235                 240

Arg Ser Ser Ile Ser Ile Leu Glu Gln Glu Lys Val Val Ala Gln Gln
            245                 250                 255

Ile Arg Gln Leu Phe Pro Lys Phe Ala Asp Thr Pro Ile Tyr Asn Asp
            260                 265                 270

Glu Ala Asp Pro Leu Val Gly Trp Ser Leu Pro Gln Pro Trp Arg Ala
            275                 280                 285

Asp Val Thr Tyr Ala Ala Met Val Val Lys Val Ile Ala Gln His Gln
            290                 295                 300

Asn Leu Leu Leu Ala Asn Thr Thr Ser Ala Phe Pro Tyr Ala Leu Leu
305                 310                 315                 320

Ser Asn Asp Asn Ala Phe Leu Ser Tyr His Pro His Pro Phe Ala Gln
                325                 330                 335

Arg Thr Leu Thr Ala Arg Phe Gln Val Asn Asn Thr Arg Pro Pro His
                340                 345                 350

Val Gln Leu Leu Arg Lys Pro Val Leu Thr Ala Met Gly Leu Leu Ala
            355                 360                 365

Leu Leu Asp Glu Glu Gln Leu Trp Ala Glu Val Ser Gln Ala Gly Thr
370                 375                 380

Val Leu Asp Ser Asn His Thr Val Gly Val Leu Ala Ser Ala His Arg
385                 390                 395                 400

Pro Gln Gly Pro Ala Asp Ala Trp Arg Ala Ala Val Leu Ile Tyr Ala
                405                 410                 415

Ser Asp Asp Thr Arg Ala His Pro Asn Arg Ser Val Ala Val Thr Leu
                420                 425                 430

Arg Leu Arg Gly Val Pro Pro Gly Pro Gly Leu Val Tyr Val Thr Arg
            435                 440                 445

Tyr Leu Asp Asn Gly Leu Cys Ser Pro Asp Gly Glu Trp Arg Arg Leu
450                 455                 460

Gly Arg Pro Val Phe Pro Thr Ala Glu Gln Phe Arg Arg Met Arg Ala
465                 470                 475                 480

Ala Glu Asp Pro Val Ala Ala Pro Arg Pro Leu Pro Ala Gly Gly
                485                 490                 495

Arg Leu Thr Leu Arg Pro Ala Leu Arg Leu Pro Ser Leu Leu Leu Val
            500                 505                 510

His Val Cys Ala Arg Pro Glu Lys Pro Pro Gly Gln Val Thr Arg Leu
            515                 520                 525

Arg Ala Leu Pro Leu Thr Gln Gly Gln Leu Val Leu Val Trp Ser Asp
530                 535                 540

Glu His Val Gly Ser Lys Cys Leu Trp Thr Tyr Glu Ile Gln Phe Ser
545                 550                 555                 560

Gln Asp Gly Lys Ala Tyr Thr Pro Val Ser Arg Lys Pro Ser Thr Phe
                565                 570                 575

Asn Leu Phe Val Phe Ser Pro Asp Thr Gly Ala Val Ser Gly Ser Tyr
                580                 585                 590

Arg Val Arg Ala Leu Asp Tyr Trp Ala Arg Pro Gly Pro Phe Ser Asp
            595                 600                 605

Pro Val Pro Tyr Leu Glu Val Pro Val Pro Arg Gly Pro Pro Ser Pro
            610                 615                 620

Gly Asn Pro Pro Glu Pro Ile Val Arg Ile Val Gly Arg Asn Gly Leu
625                 630                 635                 640
```

```
Cys Val Asp Val Arg Asp Gly Arg Phe His Asn Gly Asn Ala Ile Gln
                645                 650                 655

Leu Trp Pro Cys Lys Ser Asn Thr Asp Ala Asn Gln Leu Trp Thr Leu
        660                 665                 670

Lys Arg Asp Asn Thr Ile Arg Ser Asn Gly Lys Cys Leu Thr Thr Tyr
    675                 680                 685

Gly Tyr Ser Pro Gly Val Tyr Val Met Ile Tyr Asp Cys Asn Thr Ala
690                 695                 700

Ala Thr Asp Ala Thr Arg Trp Gln Ile Trp Asp Asn Gly Thr Ile Ile
705                 710                 715                 720

Asn Pro Arg Ser Ser Leu Val Leu Ala Ala Thr Ser Gly Asn Ser Gly
                725                 730                 735

Thr Thr Leu Thr Val Gln Thr Asn Ile Tyr Ala Val Ser Gln Gly Trp
        740                 745                 750

Leu Pro Thr Asn Asn Thr Gln Pro Phe Val Thr Thr Ile Val Gly Leu
    755                 760                 765

Tyr Gly Leu Cys Leu Gln Ala Asn Ser Gly Val Trp Ile Glu Asp
770                 775                 780

Cys Ser Ser Glu Lys Ala Glu Gln Gln Trp Ala Leu Tyr Ala Asp Gly
785                 790                 795                 800

Ser Ile Arg Pro Gln Gln Asn Arg Asp Asn Cys Leu Thr Ser Asp Ser
                805                 810                 815

Asn Ile Arg Glu Thr Val Val Lys Ile Leu Ser Cys Gly Pro Ala Ser
        820                 825                 830

Ser Gly Gln Arg Trp Met Phe Lys Asn Asp Gly Thr Ile Leu Asn Leu
    835                 840                 845

Tyr Ser Gly Leu Val Leu Asp Val Arg Ala Ser Asp Pro Ser Leu Lys
850                 855                 860

Gln Ile Ile Leu Tyr Pro Leu His Gly Asp Pro Asn Gln Ile Trp Leu
865                 870                 875                 880

Pro Leu Phe

<210> SEQ ID NO 7
<211> LENGTH: 892
<212> TYPE: PRT
<213> ORGANISM: Artificial sequence
<220> FEATURE:
<223> OTHER INFORMATION: Fusion protein

<400> SEQUENCE: 7

Glu Ala Pro His Leu Val Gln Val Asp Ala Ala Arg Ala Leu Trp Pro
1               5                   10                  15

Leu Arg Arg Phe Trp Arg Ser Thr Gly Phe Cys Pro Pro Leu Pro His
            20                  25                  30

Ser Gln Ala Asp Gln Tyr Val Leu Ser Trp Asp Gln Gln Leu Asn Leu
        35                  40                  45

Ala Tyr Val Gly Ala Val Pro His Arg Gly Ile Lys Gln Val Arg Thr
    50                  55                  60

His Trp Leu Leu Glu Leu Val Thr Thr Arg Gly Ser Thr Gly Arg Gly
65                  70                  75                  80

Leu Ser Tyr Asn Phe Thr His Leu Asp Gly Tyr Leu Asp Leu Leu Arg
                85                  90                  95

Glu Asn Gln Leu Leu Pro Gly Phe Glu Leu Met Gly Ser Ala Ser Gly
            100                 105                 110

His Phe Thr Asp Phe Glu Asp Lys Gln Gln Val Phe Glu Trp Lys Asp
```

```
                115                 120                 125
Leu Val Ser Ser Leu Ala Arg Arg Tyr Ile Gly Arg Tyr Gly Leu Ala
        130                 135                 140

His Val Ser Lys Trp Asn Phe Glu Thr Trp Asn Glu Pro Asp His His
145                 150                 155                 160

Asp Phe Asp Asn Val Ser Met Thr Met Gln Gly Phe Leu Asn Tyr Tyr
                165                 170                 175

Asp Ala Cys Ser Glu Gly Leu Arg Ala Ala Ser Pro Ala Leu Arg Leu
                180                 185                 190

Gly Gly Pro Gly Asp Ser Phe His Thr Pro Pro Arg Ser Pro Leu Ser
                195                 200                 205

Trp Gly Leu Leu Arg His Cys His Asp Gly Thr Asn Phe Phe Thr Gly
        210                 215                 220

Glu Ala Gly Val Arg Leu Asp Tyr Ile Ser Leu His Arg Lys Gly Ala
225                 230                 235                 240

Arg Ser Ser Ile Ser Ile Leu Glu Gln Glu Lys Val Val Ala Gln Gln
                245                 250                 255

Ile Arg Gln Leu Phe Pro Lys Phe Ala Asp Thr Pro Ile Tyr Asn Asp
                260                 265                 270

Glu Ala Asp Pro Leu Val Gly Trp Ser Leu Pro Gln Pro Trp Arg Ala
                275                 280                 285

Asp Val Thr Tyr Ala Ala Met Val Val Lys Val Ile Ala Gln His Gln
                290                 295                 300

Asn Leu Leu Leu Ala Asn Thr Thr Ser Ala Phe Pro Tyr Ala Leu Leu
305                 310                 315                 320

Ser Asn Asp Asn Ala Phe Leu Ser Tyr His Pro His Pro Phe Ala Gln
                325                 330                 335

Arg Thr Leu Thr Ala Arg Phe Gln Val Asn Asn Thr Arg Pro Pro His
                340                 345                 350

Val Gln Leu Leu Arg Lys Pro Val Leu Thr Ala Met Gly Leu Leu Ala
                355                 360                 365

Leu Leu Asp Glu Glu Gln Leu Trp Ala Glu Val Ser Gln Ala Gly Thr
        370                 375                 380

Val Leu Asp Ser Asn His Thr Val Gly Val Leu Ala Ser Ala His Arg
385                 390                 395                 400

Pro Gln Gly Pro Ala Asp Ala Trp Arg Ala Val Leu Ile Tyr Ala
                405                 410                 415

Ser Asp Asp Thr Arg Ala His Pro Asn Arg Ser Val Ala Val Thr Leu
                420                 425                 430

Arg Leu Arg Gly Val Pro Pro Gly Pro Gly Leu Val Tyr Val Thr Arg
                435                 440                 445

Tyr Leu Asp Asn Gly Leu Cys Ser Pro Asp Gly Glu Trp Arg Arg Leu
        450                 455                 460

Gly Arg Pro Val Phe Pro Thr Ala Glu Gln Phe Arg Arg Met Arg Ala
465                 470                 475                 480

Ala Glu Asp Pro Val Ala Ala Pro Arg Pro Leu Pro Ala Gly Gly
                485                 490                 495

Arg Leu Thr Leu Arg Pro Ala Leu Arg Leu Pro Ser Leu Leu Leu Val
                500                 505                 510

His Val Cys Ala Arg Pro Glu Lys Pro Pro Gly Gln Val Thr Arg Leu
        515                 520                 525

Arg Ala Leu Pro Leu Thr Gln Gly Gln Leu Val Leu Val Trp Ser Asp
530                 535                 540
```

Glu His Val Gly Ser Lys Cys Leu Trp Thr Tyr Glu Ile Gln Phe Ser
545                 550                 555                 560

Gln Asp Gly Lys Ala Tyr Thr Pro Val Ser Arg Lys Pro Ser Thr Phe
            565                 570                 575

Asn Leu Phe Val Phe Ser Pro Asp Thr Gly Ala Val Ser Gly Ser Tyr
        580                 585                 590

Arg Val Arg Ala Leu Asp Tyr Trp Ala Arg Pro Gly Pro Phe Ser Asp
    595                 600                 605

Pro Val Pro Tyr Leu Glu Val Pro Val Pro Arg Gly Pro Pro Ser Pro
610                 615                 620

Gly Asn Pro Gly Glu Thr Ser Thr Leu Arg Thr Ser Phe Thr Arg Asn
625                 630                 635                 640

Ile Val Gly Arg Asp Gly Leu Cys Val Asp Val Arg Asn Gly Tyr Asp
                645                 650                 655

Thr Asp Gly Thr Pro Leu Gln Leu Trp Pro Cys Gly Thr Gln Arg Asn
            660                 665                 670

Gln Arg Trp Thr Phe Asp Ser Asp Asp Thr Ile Arg Ser Met Gly Lys
        675                 680                 685

Cys Met Thr Ala Asn Gly Leu Asn Asn Gly Ser Asn Ile Val Ile Phe
690                 695                 700

Asn Cys Ser Thr Ala Ala Glu Asn Ala Ile Lys Trp Glu Val Pro Ile
705                 710                 715                 720

Asp Gly Ser Ile Ile Asn Pro Ser Ser Gly Leu Val Met Thr Ala Pro
                725                 730                 735

Arg Ala Ala Ser Arg Thr Ile Leu Leu Leu Glu Asp Asn Ile Tyr Ala
            740                 745                 750

Ala Ser Gln Gly Trp Thr Val Thr Asn Asn Val Lys Pro Ile Val Ala
        755                 760                 765

Ser Ile Val Gly Tyr Lys Glu Met Cys Leu Gln Ser Asn Gly Glu Asn
770                 775                 780

Asn Gly Val Trp Met Glu Asp Cys Glu Ala Thr Ser Leu Gln Gln Gln
785                 790                 795                 800

Trp Ala Leu Tyr Gly Asp Arg Thr Ile Arg Val Asn Ser Thr Arg Gly
                805                 810                 815

Leu Cys Val Thr Thr Asn Gly Tyr Asn Ser Lys Asp Leu Ile Ile Ile
            820                 825                 830

Leu Lys Cys Gln Gly Leu Pro Ser Gln Arg Trp Phe Phe Asn Ser Asp
        835                 840                 845

Gly Ala Ile Val Asn Pro Lys Ser Arg His Val Met Asp Val Arg Ala
850                 855                 860

Ser Asn Val Ser Leu Arg Glu Ile Ile Ile Phe Pro Ala Thr Gly Asn
865                 870                 875                 880

Pro Asn Gln Gln Trp Val Thr Gln Val Leu Pro Ser
                885                 890

<210> SEQ ID NO 8
<211> LENGTH: 490
<212> TYPE: PRT
<213> ORGANISM: Artificial sequence
<220> FEATURE:
<223> OTHER INFORMATION: Fusion protein

<400> SEQUENCE: 8

Val Arg Ser Ser Lys Asn Val Ile Lys Glu Phe Met Arg Phe Lys Val
1               5                   10                  15

-continued

```
Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly His Tyr Leu Val Glu
            165                 170                 175

Phe Lys Ser Ile Tyr Met Ala Lys Lys Pro Val Gln Leu Pro Gly Tyr
        180                 185                 190

Tyr Tyr Val Asp Ser Lys Leu Asp Ile Thr Ser His Asn Glu Asp Tyr
    195                 200                 205

Thr Ile Val Glu Gln Tyr Glu Arg Thr Glu Gly Arg His His Leu Phe
210                 215                 220

Leu Gly Glu Thr Ser Thr Leu Arg Thr Ser Phe Thr Arg Asn Ile Val
225                 230                 235                 240

Gly Arg Asp Gly Leu Cys Val Asp Val Arg Asn Gly Tyr Asp Thr Asp
            245                 250                 255

Gly Thr Pro Leu Gln Leu Trp Pro Cys Gly Thr Gln Arg Asn Gln Arg
        260                 265                 270

Trp Thr Phe Asp Ser Asp Asp Thr Ile Arg Ser Met Gly Lys Cys Met
    275                 280                 285

Thr Ala Asn Gly Leu Asn Asn Gly Ser Asn Ile Val Ile Phe Asn Cys
290                 295                 300

Ser Thr Ala Ala Glu Asn Ala Ile Lys Trp Glu Val Pro Ile Asp Gly
305                 310                 315                 320

Ser Ile Ile Asn Pro Ser Ser Gly Leu Val Met Thr Ala Pro Arg Ala
                325                 330                 335

Ala Ser Arg Thr Ile Leu Leu Leu Glu Asp Asn Ile Tyr Ala Ala Ser
            340                 345                 350

Gln Gly Trp Thr Val Thr Asn Asn Val Lys Pro Ile Val Ala Ser Ile
        355                 360                 365

Val Gly Tyr Lys Glu Met Cys Leu Gln Ser Asn Gly Glu Asn Asn Gly
    370                 375                 380

Val Trp Met Glu Asp Cys Glu Ala Thr Ser Leu Gln Gln Gln Trp Ala
385                 390                 395                 400

Leu Tyr Gly Asp Arg Thr Ile Arg Val Asn Ser Thr Arg Gly Leu Cys
                405                 410                 415

Val Thr Thr Asn Gly Tyr Asn Ser Lys Asp Leu Ile Ile Ile Leu Lys
            420                 425                 430
```

```
Cys Gln Gly Leu Pro Ser Gln Arg Trp Phe Phe Asn Ser Asp Gly Ala
            435                 440                 445

Ile Val Asn Pro Lys Ser Arg His Val Met Asp Val Arg Ala Ser Asn
    450                 455                 460

Val Ser Leu Arg Glu Ile Ile Ile Phe Pro Ala Thr Gly Asn Pro Asn
465                 470                 475                 480

Gln Gln Trp Val Thr Gln Val Leu Pro Ser
                485                 490

<210> SEQ ID NO 9
<211> LENGTH: 747
<212> TYPE: PRT
<213> ORGANISM: Artificial sequence
<220> FEATURE:
<223> OTHER INFORMATION: Fusion protein

<400> SEQUENCE: 9

Gly Glu Thr Ser Thr Leu Arg Thr Ser Phe Thr Arg Asn Ile Val Gly
1               5                   10                  15

Arg Asp Gly Leu Cys Val Asp Val Arg Asn Gly Tyr Asp Thr Asp Gly
                20                  25                  30

Thr Pro Leu Gln Leu Trp Pro Cys Gly Thr Gln Arg Asn Gln Arg Trp
            35                  40                  45

Thr Phe Asp Ser Asp Thr Ile Arg Ser Met Gly Lys Cys Met Thr
    50                  55                  60

Ala Asn Gly Leu Asn Asn Gly Ser Asn Ile Val Ile Phe Asn Cys Ser
65              70                  75                  80

Thr Ala Ala Glu Asn Ala Ile Lys Trp Glu Val Pro Ile Asp Gly Ser
                85                  90                  95

Ile Ile Asn Pro Ser Ser Gly Leu Val Met Thr Ala Pro Arg Ala Ala
            100                 105                 110

Ser Arg Thr Ile Leu Leu Leu Glu Asp Asn Ile Tyr Ala Ala Ser Gln
        115                 120                 125

Gly Trp Thr Val Thr Asn Asn Val Lys Pro Ile Val Ala Ser Ile Val
    130                 135                 140

Gly Tyr Lys Glu Met Cys Leu Gln Ser Asn Gly Glu Asn Asn Gly Val
145                 150                 155                 160

Trp Met Glu Asp Cys Glu Ala Thr Ser Leu Gln Gln Gln Trp Ala Leu
                165                 170                 175

Tyr Gly Asp Arg Thr Ile Arg Val Asn Ser Thr Arg Gly Leu Cys Val
            180                 185                 190

Thr Thr Asn Gly Tyr Asn Ser Lys Asp Leu Ile Ile Ile Leu Lys Cys
        195                 200                 205

Gln Gly Leu Pro Ser Gln Arg Trp Phe Phe Asn Ser Asp Gly Ala Ile
    210                 215                 220

Val Asn Pro Lys Ser Arg His Val Met Asp Val Arg Ala Ser Asn Val
225                 230                 235                 240

Ser Leu Arg Glu Ile Ile Ile Phe Pro Ala Thr Gly Asn Pro Asn Gln
                245                 250                 255

Gln Trp Val Thr Gln Val Leu Pro Ser Arg Pro Arg Asn Ala Leu Leu
            260                 265                 270

Leu Leu Ala Asp Asp Gly Gly Phe Glu Ser Gly Ala Tyr Asn Asn Ser
        275                 280                 285

Ala Ile Ala Thr Pro His Leu Asp Ala Leu Ala Arg Arg Ser Leu Leu
    290                 295                 300
```

```
Phe Arg Asn Ala Phe Thr Ser Val Ser Ser Cys Ser Pro Ser Arg Ala
305                 310                 315                 320

Ser Leu Leu Thr Gly Leu Pro Gln His Gln Asn Gly Met Tyr Gly Leu
                325                 330                 335

His Gln Asp Val His His Phe Asn Ser Phe Asp Lys Val Arg Ser Leu
            340                 345                 350

Pro Leu Leu Ser Gln Ala Gly Val Arg Thr Gly Ile Ile Gly Lys
        355                 360                 365

Lys His Val Gly Pro Glu Thr Val Tyr Pro Phe Asp Phe Ala Tyr Thr
    370                 375                 380

Glu Glu Asn Gly Ser Val Leu Gln Val Gly Arg Asn Ile Thr Arg Ile
385                 390                 395                 400

Lys Leu Leu Val Arg Lys Phe Leu Gln Thr Gln Asp Asp Arg Pro Phe
                405                 410                 415

Phe Leu Tyr Val Ala Phe His Asp Pro His Arg Cys Gly His Ser Gln
                420                 425                 430

Pro Gln Tyr Gly Thr Phe Cys Glu Lys Phe Gly Asn Gly Glu Ser Gly
        435                 440                 445

Met Gly Arg Ile Pro Asp Trp Thr Pro Gln Ala Tyr Asp Pro Leu Asp
450                 455                 460

Val Leu Val Pro Tyr Phe Val Pro Asn Thr Pro Ala Ala Arg Ala Asp
465                 470                 475                 480

Leu Ala Ala Gln Tyr Thr Thr Val Gly Arg Met Asp Gln Gly Val Gly
                485                 490                 495

Leu Val Leu Gln Glu Leu Arg Asp Ala Gly Val Leu Asn Asp Thr Leu
        500                 505                 510

Val Ile Phe Thr Ser Asp Asn Gly Ile Pro Phe Pro Ser Gly Arg Thr
    515                 520                 525

Asn Leu Tyr Trp Pro Gly Thr Ala Glu Pro Leu Leu Val Ser Ser Pro
530                 535                 540

Glu His Pro Lys Arg Trp Gly Gln Val Ser Glu Ala Tyr Val Ser Leu
545                 550                 555                 560

Leu Asp Leu Thr Pro Thr Ile Leu Asp Trp Phe Ser Ile Pro Tyr Pro
                565                 570                 575

Ser Tyr Ala Ile Phe Gly Ser Lys Thr Ile His Leu Thr Gly Arg Ser
            580                 585                 590

Leu Leu Pro Ala Leu Glu Ala Glu Pro Leu Trp Ala Thr Val Phe Gly
        595                 600                 605

Ser Gln Ser His His Glu Val Thr Met Ser Tyr Pro Met Arg Ser Val
610                 615                 620

Gln His Arg His Phe Arg Leu Val His Asn Leu Asn Phe Lys Met Pro
625                 630                 635                 640

Phe Pro Ile Asp Gln Asp Phe Tyr Val Ser Pro Thr Phe Gln Asp Leu
                645                 650                 655

Leu Asn Arg Thr Thr Ala Gly Gln Pro Thr Gly Trp Tyr Lys Asp Leu
            660                 665                 670

Arg His Tyr Tyr Tyr Arg Ala Arg Trp Glu Leu Tyr Asp Arg Ser Arg
        675                 680                 685

Asp Pro His Glu Thr Gln Asn Leu Ala Thr Asp Pro Arg Phe Ala Gln
    690                 695                 700

Leu Leu Glu Met Leu Arg Asp Gln Leu Ala Lys Trp Gln Trp Glu Thr
705                 710                 715                 720

His Asp Pro Trp Val Cys Ala Pro Asp Gly Val Leu Glu Glu Lys Leu
```

Ser Pro Gln Cys Gln Pro Leu His Asn Glu Leu
            740                 745

<210> SEQ ID NO 10
<211> LENGTH: 738
<212> TYPE: PRT
<213> ORGANISM: Artificial sequence
<220> FEATURE:
<223> OTHER INFORMATION: Fusion protein

<400> SEQUENCE: 10

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
        35                  40                  45

Ser Cys Ser Pro Ser Arg Ala Ser Leu Leu Thr Gly Leu Pro Gln His
    50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Leu Ser Gln Ala Gly Val
                85                  90                  95

Arg Thr Gly Ile Ile Gly Lys Lys His Val Gly Pro Glu Thr Val Tyr
            100                 105                 110

Pro Phe Asp Phe Ala Tyr Thr Glu Glu Asn Gly Ser Val Leu Gln Val
        115                 120                 125

Gly Arg Asn Ile Thr Arg Ile Lys Leu Leu Val Arg Lys Phe Leu Gln
    130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
        195                 200                 205

Thr Pro Ala Ala Arg Ala Asp Leu Ala Ala Gln Tyr Thr Thr Val Gly
    210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
        275                 280                 285

Ser Glu Ala Tyr Val Ser Leu Leu Asp Leu Thr Pro Thr Ile Leu Asp
    290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met

```
                340             345             350
Ser Tyr Pro Met Arg Ser Val Gln His Arg His Phe Arg Leu Val His
            355                 360                 365

Asn Leu Asn Phe Lys Met Pro Phe Pro Ile Asp Gln Asp Phe Tyr Val
        370                 375                 380

Ser Pro Thr Phe Gln Asp Leu Leu Asn Arg Thr Ala Gly Gln Pro
385                 390                 395                 400

Thr Gly Trp Tyr Lys Asp Leu Arg His Tyr Tyr Arg Ala Arg Trp
                405                 410                 415

Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
        435                 440                 445

Ala Lys Trp Gln Trp Glu Thr His Asp Pro Trp Val Cys Ala Pro Asp
    450                 455                 460

Gly Val Leu Glu Glu Lys Leu Ser Pro Gln Cys Gln Pro Leu His Asn
465                 470                 475                 480

Glu Leu Pro Glu Pro Ile Val Arg Ile Val Gly Arg Asn Gly Leu Cys
                485                 490                 495

Val Asp Val Arg Asp Gly Arg Phe His Asn Gly Asn Ala Ile Gln Leu
            500                 505                 510

Trp Pro Cys Lys Ser Asn Thr Asp Ala Asn Gln Leu Trp Thr Leu Lys
        515                 520                 525

Arg Asp Asn Thr Ile Arg Ser Asn Gly Lys Cys Leu Thr Thr Tyr Gly
    530                 535                 540

Tyr Ser Pro Gly Val Tyr Val Met Ile Tyr Asp Cys Asn Thr Ala Ala
545                 550                 555                 560

Thr Asp Ala Thr Arg Trp Gln Ile Trp Asp Asn Gly Thr Ile Ile Asn
                565                 570                 575

Pro Arg Ser Ser Leu Val Leu Ala Ala Thr Ser Gly Asn Ser Gly Thr
            580                 585                 590

Thr Leu Thr Val Gln Thr Asn Ile Tyr Ala Val Ser Gln Gly Trp Leu
        595                 600                 605

Pro Thr Asn Asn Thr Gln Pro Phe Val Thr Thr Ile Val Gly Leu Tyr
    610                 615                 620

Gly Leu Cys Leu Gln Ala Asn Ser Gly Gln Val Trp Ile Glu Asp Cys
625                 630                 635                 640

Ser Ser Glu Lys Ala Glu Gln Gln Trp Ala Leu Tyr Ala Asp Gly Ser
                645                 650                 655

Ile Arg Pro Gln Gln Asn Arg Asp Asn Cys Leu Thr Ser Asp Ser Asn
            660                 665                 670

Ile Arg Glu Thr Val Val Lys Ile Leu Ser Cys Gly Pro Ala Ser Ser
        675                 680                 685

Gly Gln Arg Trp Met Phe Lys Asn Asp Gly Thr Ile Leu Asn Leu Tyr
    690                 695                 700

Ser Gly Leu Val Leu Asp Val Arg Ala Ser Asp Pro Ser Leu Lys Gln
705                 710                 715                 720

Ile Ile Leu Tyr Pro Leu His Gly Asp Pro Asn Gln Ile Trp Leu Pro
                725                 730                 735

Leu Phe

<210> SEQ ID NO 11
<211> LENGTH: 28
```

-continued

```
<212> TYPE: PRT
<213> ORGANISM: Artificial sequence
<220> FEATURE:
<223> OTHER INFORMATION: potatin signal sequence

<400> SEQUENCE: 11

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp
            20                  25
```